(12) United States Patent
Hirota et al.

(10) Patent No.: US 7,901,498 B2
(45) Date of Patent: Mar. 8, 2011

(54) TRISAZO COMPOUND, INK COMPOSITION, PRINTING METHOD AND COLORED PRODUCT

(75) Inventors: Koji Hirota, Tokyo (JP); Takahiko Matsui, Tokyo (JP); Takashi Yoshimoto, Tokyo (JP); Shinsuke Shimizu, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/734,655

(22) PCT Filed: Nov. 25, 2008

(86) PCT No.: PCT/JP2008/003449
§ 371 (c)(1),
(2), (4) Date: May 14, 2010

(87) PCT Pub. No.: WO2009/069279
PCT Pub. Date: Jun. 4, 2009

(65) Prior Publication Data
US 2010/0309246 A1    Dec. 9, 2010

(30) Foreign Application Priority Data
Nov. 27, 2007   (JP) .................................. 2007-306268

(51) Int. Cl.
*C09D 11/02* (2006.01)
*C09B 31/16* (2006.01)

(52) U.S. Cl. .................... 106/31.5; 534/752; 534/755
(58) Field of Classification Search ............... 106/31.5; 534/752, 755; 428/195.1; 347/100
See application file for complete search history.

(56) References Cited

U.S. PATENT DOCUMENTS

| | | | |
|---|---|---|---|
| 4,012,371 A * | 3/1977 | Roueche et al. | 534/752 |
| 4,565,424 A * | 1/1986 | Huffman et al. | 534/755 |
| 7,217,803 B2 * | 5/2007 | Feiler et al. | 534/752 |
| 7,550,037 B2 * | 6/2009 | Mafune et al. | 106/31.48 |
| 2006/0053571 A1 * | 3/2006 | Feiler et al. | 8/512 |
| 2007/0062409 A1 * | 3/2007 | Mistry et al. | 106/31.5 |
| 2009/0011130 A1 * | 1/2009 | Mafune et al. | 106/31.48 |
| 2009/0062545 A1 * | 3/2009 | Matsui et al. | 106/31.48 |

FOREIGN PATENT DOCUMENTS

| DE | 2 004 488 A1 | 8/1971 |
|---|---|---|
| JP | 2006-509068 A | 3/2006 |
| JP | 2007-517082 A | 6/2007 |
| WO | WO 2008/096697 A1 | 8/2008 |

OTHER PUBLICATIONS

International Search Report dated Feb. 17, 2009.

* cited by examiner

Primary Examiner — Helene Klemanski
(74) Attorney, Agent, or Firm — Nields, Lemack & Frame, LLC

(57) ABSTRACT

The present invention relates to a trisazo compound represented by the following formula (1):

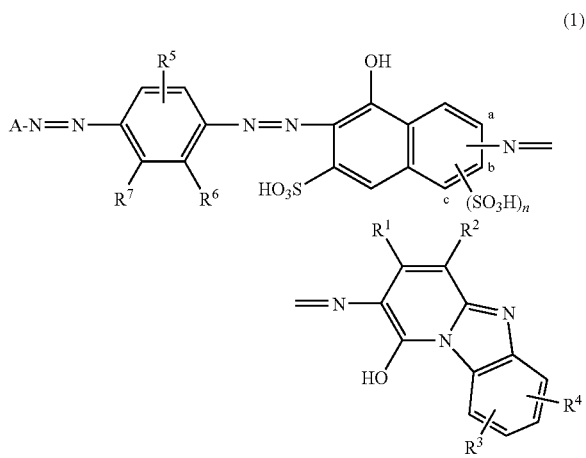

wherein, n represents 0 or 1, the group A represents a substituted heterocyclic group, $R^1$ represents a C1-C4 alkyl group which may be substituted or the like, $R^2$ represents a cyano group or the like, $R^3$ and $R^4$ each independently represent a hydrogen atom, a sulfo group or the like, $R^5$ to $R^7$ each independently represent a hydrogen atom, a C1-C4 alkyl group which may be substituted, a C1-C4 alkoxy group which may be substituted or the like, respectively or salt thereof. Said trisazo compound or salt thereof provides a coloring matter compound for black ink and an ink composition thereof where they have high solubility in medium where water is a principal component, their aqueous solution and ink having high concentration is stable even when stored for a long period of time, printed images therewith have very high density, no bronzing is caused on the images printed even with their high concentration solution, and they give black recorded images excellent in fastness, particularly in both light fastness and ozone gas fastness.

19 Claims, No Drawings

TRISAZO COMPOUND, INK COMPOSITION, PRINTING METHOD AND COLORED PRODUCT

TECHNICAL FIELD

The present invention relates to a novel trisazo compound or a salt thereof, an ink composition containing these and a colored product colored therewith.

BACKGROUND ART

As for the recording method by means of an inkjet printer which is one of the typical methods among various color recording methods, ink droplets are generated and adhered onto various record-receiving materials (such as paper, film and cloth) to perform recording. This method has been rapidly prevailing lately and is expected to continue growing remarkably in the future because of features such as quietness with a little noise generation due to no direct contact of a recording head with a record-receiving material and as easiness in downsizing and speeding up. Conventionally, as an ink for fountain pens, felt-tip pens or the like and as an ink for inkjet recording, inks where a water-soluble dye is dissolved in an aqueous medium have been used. In these water-based inks, a water-soluble organic solvent is generally added to prevent ink from clogging at a pen tip or an inkjet nozzle. These inks are required to provide recorded images with sufficient density, not to clog at a pen tip or a nozzle, to dry quickly on a record-receiving material, to bleed less, to have excellent storage stability, and so on. In addition, the water-soluble coloring matter to be used is required to have high solubility particularly in water and in water-soluble organic solvents to be added to the inks. Further, recorded images formed are required to have fastnesses such as water fastness, light fastness, ozone gas fastness and moisture fastness.

The above described ozone gas fastness means durability against the phenomenon that ozone gas existing in the air and having oxidizing effects acts on coloring matter in recorded paper, leading to discoloration or fading of printed images. Besides ozone gas, the oxidizing gas having this kind of action includes NOx, SOx and the like. However, among these oxidizing gases, ozone gas is regarded as the main causative matter which drives the discoloration or fading phenomenon of inkjet-printed images.

In many ink receiving layers to be provided on the surface of special paper for photo quality inkjet, materials such as porous white inorganic substance are used in order to dry ink sooner and to reduce ink bleeding on high image quality. On such recorded paper, discoloration or fading caused by ozone gas is prominently observed. Discoloration or fading phenomenon caused by this oxidizing gas, particularly by ozone gas, is characteristic on inkjet images, so improvement of ozone gas fastness is one of the most important problems in inkjet printing method.

In order to expand the application field of the printing method using ink in the future, ink compositions to be used for inkjet printing and colored products colored therewith are strongly desired to have light fastness, ozone gas fastness, moisture fastness and water fastness which are further improved.

Inks having different hues are prepared from different coloring matters, and among them, black ink is an important ink to be used for both mono- and full-color images. Many coloring matters have been proposed as a coloring matter for these black inks, but any of them has yet to provide a product sufficiently satisfying the market requirements. Many of the proposed coloring matters are azo coloring matter. Among them, disazo coloring matter such as C.I.Food Black 2 has problems such as low optical density of image, poor water and moisture fastnesses, and insufficient light and gas (ozone) fastnesses. Polyazo coloring matter where the conjugated system is extended has generally problems such that water-solubility is low, bronzing phenomenon that recorded image partially has metallic luster is easily caused, and such that its light and gas fastnesses are not sufficient. Further, among many metal-containing azo coloring matters proposed, some have good light fastness, but they similarly have problems such that they are not desirable in terms of biological safety and environmental problems because it contains metal ion, and in addition to that, they are also extremely low in ozone gas fastness.

Black coloring matter for inkjet improved in ozone gas fastness which is the most important problem in recent years includes, for example, the compounds described in Patent Literatures 1 to 3. These compounds do not have ozone gas fastness satisfying the market requirements or sufficient light fastness. In addition, Patent Literatures 4 to 7 describe azo compounds having a benzimidazolopyridone structure in a molecule. Patent Literature 4 discloses a monoazo or disazo coloring matter compound which is soluble in organic solvents. Patent Literature 5 discloses a trisazo compound. These trisazo compounds are a compound having a symmetrical structure where the both ends of the linking group comprising a trisazo structure bear two benzimidazolopyridone structures. Further, none of Patent Literatures 4 to 7 discloses use examples of the black compounds for inkjet ink. Examples of a black trisazo compound for inkjet not having a benzimidazolopyridone structure and having ozone gas fastness include the compound described in Patent Literature 8.

[Patent Literature 1] JP 2003-183545 A
[Patent Literature 2] JP 2003-201412 A
[Patent Literature 3] JP 2007-517082 A
[Patent Literature 4] WO 2004/050768
[Patent Literature 5] DE Patent 2004488
[Patent Literature 6] DE Patent 2023295
[Patent Literature 7] JP H05-134435 A
[Patent Literature 8] WO 2005/054374

DISCLOSURE OF THE INVENTION

Problems to be Solved by the Invention

It is an object of the present invention to provide; a coloring matter (compound) for black ink having such characteristics that its solubility in medium where water is the principal component is high, its aqueous solution or ink with a high concentration is stable even after storage for a long period of time, the density of images printed therewith is very high, bronzing is not caused on the images even when its solution with a high concentration is printed on inkjet special paper for photo quality, it also gives black recorded images excellent in fastnesses, particularly both light fastness and ozone gas fastness, and in addition, the synthesis thereof is easy and inexpensive; an ink composition containing it, particularly a black ink composition for inkjet; a method for inkjet printing with said ink composition; and a colored product with said coloring matter.

Means of Solving the Problems

The present inventors have intensively studied to solve such problems as described above and found that a certain trisazo compound can solve the above problems, and thus completed the present invention.

That is, the present invention relates to:

(1)
A trisazo compound represented by the following formula (1) or a salt thereof:

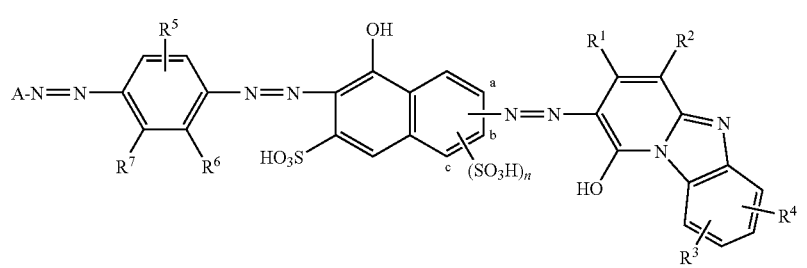
(1)

[wherein, n is 0 or 1,
R[1] represents a carboxy group; an unsubstituted C1-C4 alkyl group; a C1-C4 alkyl group substituted by a carboxy group; an unsubstituted phenyl group; or a phenyl group substituted by a sulfo group,
R[2] represents a cyano group; a carbamoyl group; or a carboxy group,
R[3] and R[4] each independently represent a hydrogen atom; a chlorine atom; a sulfo group; an unsubstituted C1-C4 alkyl group; or an unsubstituted C1-C4 alkoxy group,
R[5] to R[7] each independently represent a hydrogen atom; a chlorine atom; a hydroxy group; a sulfo group; a carboxy group; a sulfamoyl group; a carbamoyl group; an unsubstituted C1-C4 alkyl group; an unsubstituted C1-C4 alkoxy group; a C1-C4 alkoxy group substituted by a hydroxy group, an unsubstituted C1-C4 alkoxy group, a hydroxy C1-C4 alkoxy group, a sulfo group or a carboxy group; a mono- or di-unsubstituted C1-C4 alkylamino group; a mono- or di-C1-C4 alkylamino group substituted by a hydroxy group, a sulfo group or a carboxy group; an unsubstituted C1-C4 alkylcarbonylamino group; a C1-C4 alkylcarbonylamino group substituted by a hydroxy group or a carboxy group; an N'-(unsubstituted C1-C4 alkyl)ureide group; an N'-(a C1-C4 alkyl substituted by a hydroxy group, a sulfo group or a carboxy group)ureide group; an unsubstituted phenylamino group; a phenylamino group where the benzene ring is substituted by a chlorine atom, an unsubstituted C1-C4 alkyl group, a nitro group, a sulfo group or a carboxy group; an unsubstituted benzoylamino group; a benzoylamino group where the benzene ring is substituted by a chlorine atom, an unsubstituted C1-C4 alkyl group, a nitro group, a sulfo group or a carboxy group; an unsubstituted phenylsulfonylamino group; or a phenylsulfonylamino group where the benzene ring is substituted by a chlorine atom, an unsubstituted C1-C4 alkyl group, a nitro group, a sulfo group or a carboxy group, the substitution position of the azo group of the naphthalene ring to which the benzimidazolopyridine ring substituted by R[1] to R[4] is bonded via the azo group is a or b; and the substitution position of the sulfo group by which said naphthalene ring is substituted is b or c, provided that the position is not overlapped with the substitution position of the above azo group, and the group A is a substituted heterocyclic group represented by the following formula (2) or (3):

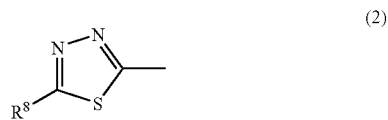
(2)

(wherein, R[8] represents a mercapto group; an unsubstituted C1-C4 alkylthio group; or a C1-C4 alkylthio group substituted by a hydroxy group, an unsubstituted C1-C4 alkoxy group, a hydroxy C1-C4 alkoxy group, a sulfo group or a carboxy group)

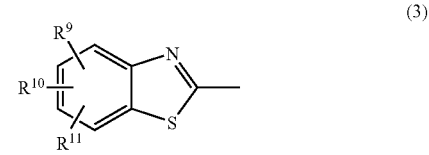
(3)

(wherein, R[9] to R[11] each independently represent a hydrogen atom; a chlorine atom; a carboxy group; a sulfo group; a nitro group; a hydroxy group; a carbamoyl group; a sulfamoyl group; an unsubstituted C1-C4 alkyl group; an unsubstituted C1-C4 alkoxy group; a C1-C4 alkoxy group substituted by a hydroxy group, an unsubstituted C1-C4 alkoxy group, a sulfo group or a carboxy group; an unsubstituted C1-C4 alkylsulfonyl group; a C1-C4 alkylsulfonyl group substituted by a hydroxy group, a sulfo group or a carboxy group; an unsubstituted phenylsulfonyl group; or a phenylsulfonyl group where the benzene ring is substituted by a chlorine atom, an unsubstituted C1-C4 alkyl group, a nitro group, a sulfo group or a carboxy group)], (2)

The trisazo compound or a salt thereof according to the above (1), which is represented by the following formula (4):

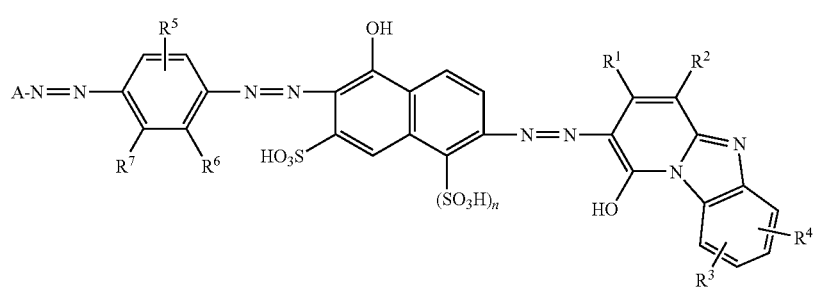
(4)

(wherein, n, the group A and $R^1$ to $R^7$ have the same meanings as in the formula (1)), (3)

The trisazo compound or a salt thereof according to the above (1) or (2), which is represented by the following formula (5):

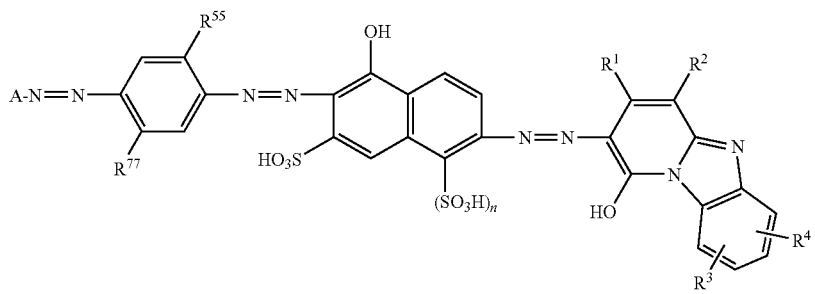

(5)

(wherein, n, the group A and $R^1$ to $R^4$ have the same meanings as in the formula (1), $R^{55}$ represents a sulfo C1-C4 alkoxy group, and $R^{77}$ represents a hydrogen atom, a methyl group or an ethyl group), (4)

The trisazo compound or a salt thereof according to any one of the above (1) to (3), wherein the group A is represented by the formula (2), $R^8$ is a sulfo C1-C4 alkylthio group or a carboxy C1-C4 alkylthio group, (5)

The trisazo compound or a salt thereof according to any one of the above (1) to (3), wherein the group A is represented by the formula (3), $R^9$ to $R^{11}$ are each independently a hydrogen atom, a chlorine atom, a carboxy group, a sulfo group, a nitro group, an unsubstituted C1-C4 alkyl group, an unsubstituted C1-C4 alkoxy group or an unsubstituted C1-C4 alkylsulfonyl group, (6)

The trisazo compound or a salt thereof according to any one of the above (1) to (5), wherein $R^1$ is a methyl group, $R^2$ is a cyano group or a carbamoyl group, $R^3$ is a hydrogen atom, and $R^4$ is a sulfo group, (7)

The trisazo compound or a salt thereof according to the above (1) or (3), wherein the group A is a substituted heterocyclic group represented by the formula (2) or the formula (3), $R^8$ of the formula (2) is a sulfo C1-C4 alkylthio group or a carboxy C1-C4 alkylthio group, and $R^9$ to $R^{11}$ of the formula (3) are each independently a hydrogen atom, a chlorine atom, a carboxy group, a sulfo group, a nitro group, an unsubstituted C1-C4 alkyl group, an unsubstituted C1-C4 alkoxy group or an unsubstituted C1-C4 alkylsulfonyl group, (8)

The trisazo compound or a salt thereof according to the above (7), wherein $R^1$ is a methyl group, $R^2$ is a cyano group or a carbamoyl group, $R^3$ is a hydrogen atom and $R^4$ is a sulfo group, (9)

The trisazo compound or a salt thereof according to any one of the above (1) to (3) and (5) to (8), wherein n is 1, $R^1$ is a methyl group, $R^2$ is a cyano group, $R^3$ is a hydrogen atom, $R^4$ is a sulfo group, $R^5$ is a sulfopropoxy group, $R^6$ is a hydrogen atom, $R^7$ is a methyl group, the group A is the formula (3), $R^9$ to $R^{11}$ are each independently a hydrogen atom, a chlorine atom, a carboxy group, a sulfo group, a nitro group, a methyl group, a methoxy group or a methylsulfonyl group, (10)

An ink composition characterized by containing at least one kind of the trisazo compound or a salt thereof according to any one of the above (1) to (9) as a coloring matter, (11)

A method for inkjet printing characterized by adhering an ink composition containing at least one kind of the trisazo compound or a salt thereof according to any one of the above (1) to (9) on a record-receiving material by inkjet, (12)

The method for inkjet printing according to the above (11), wherein the record-receiving material in the inkjet printing is a communication sheet, (13)

The method for inkjet printing according to the above (12), wherein the communication sheet is a sheet containing a porous white inorganic substance, (14)

An inkjet printer comprising a container containing an ink composition containing at least one kind of the trisazo compound or a salt thereof according to any one of the above (1) to (9), (15)

A colored product colored with the trisazo compound or a salt thereof according to any one of the above (1) to (9).

(16)

The trisazo compound or a salt thereof according to the above (1), wherein:
$R^1$ is an unsubstituted C1-C4 alkyl group or an unsubstituted phenyl group,
$R^2$ is a cyano group or a carbamoyl group,
$R^3$ is a hydrogen atom,
$R^4$ is a sulfo group,
$R^5$ to $R^7$ are each independently a hydrogen atom; a sulfo group; an unsubstituted C1-C4 alkyl group; an unsubstituted C1-C4 alkoxy group; a C1-C4 alkoxy group substituted by a hydroxy group, a carboxy group or a sulfo group; an unsubstituted C1-C4 dialkylamino group; a dialkylamino group substituted by a carboxy group, a sulfo group or a hydroxy group; an unsubstituted C1-C4 alkylcarbonylamino group; N'-C1-C4 alkylureide group substituted by a sulfo group or a carboxy group; or an unsubstituted benzoylamino group,
$R^8$ is a C1-C4 alkylthio group substituted by a sulfo group or a carboxy group, $R^9$ to $R^{11}$ are each independently a hydrogen atom; a chlorine atom; a carboxy group; a sulfo group; a nitro group; an unsubstituted C1-C4 alkyl group; an unsubstituted C1-C4 alkoxy group; or unsubstituted C1-C4 alkylsulfonyl group, and any two of $R^5$ to $R^7$ are groups other than a hydrogen atom.

(17)

The trisazo compound or a salt thereof according to the above (7), wherein n is 1, $R^1$ is an alkyl group having 1 to 4 carbon atoms, $R^2$ is a cyano group, any one of $R^3$ and $R^4$ is a hydrogen atom and the other is a sulfo group, $R^8$ of the formula (2) is a sulfo C1-C4 alkylthio group, $R^9$ to $R^{11}$ of the formula (3) are each independently a hydrogen atom, a chlorine atom, a sulfo group, a nitro group, an unsubstituted C1-C4 alkoxy group or an unsubstituted C1-C4 alkylsulfonyl group, at least one of $R^9$ to $R^{11}$ is a sulfo group, either of the rest is a hydrogen atom and the other is a hydrogen atom or a group other than a hydrogen atom.

(18)

The trisazo compound or a salt thereof according to the above (17), wherein the group A is the formula (3), at least one of $R^9$ to $R^{11}$ is a sulfo group, either of the rest is a hydrogen atom and the other is a group other than a hydrogen atom.

(19)

The trisazo compound or a salt thereof according to the above (18), wherein the group other than a hydrogen atom is a sulfo group or an unsubstituted C1-C4 alkoxy group.

Effect of the Invention

When the trisazo compound of the present invention is used alone for coloring and the like, excellent black colored product is obtained, whereby said compound is useful as a black coloring matter. When the trisazo compound of the present invention is used as a black coloring matter, said black coloring matter is excellent in water-solubility, whereby the filterability thereof through a membrane filter in the process of producing ink compositions is good, and the ink composition or inks containing this are good in storage stability and jet stability. Therefore, the ink composition of the present invention containing this trisazo compound is free from crystal precipitation, change in physical properties and change in color after storage for a long period of time, and it does not cause clogging at the discharging outlet in various inkjet printing methods. In addition, the ink composition containing the trisazo compound of the present invention is suitably used for inkjet printing, writing tools and the like. When said ink composition is used for recording on plain paper and inkjet special paper, the print density of recorded images is very high, and even when a high concentration solution thereof is printed, bronzing is not caused on images. Further, the various fastnesses thereof, particularly both light fastness and ozone gas fastness, are excellent.

Furthermore, the ink composition of the present invention is excellent in various fastnesses by using together with ink compositions where magenta, cyan and yellow coloring matters are used, and it allows inkjet printing of full color excellent in storage stability. The ink composition of the present invention is thus extremely useful as a black ink particularly for inkjet printing.

BEST MODE FOR CARRYING OUT THE INVENTION

Hereinafter, the present invention will be specifically explained.

The trisazo compound represented by the formula (1) has a tautomer, and isomers represented by the following formulas (6) to (10) other than the formula (1) and the like may exist. These tautomers are included in the present invention. Hereinafter, the trisazo compound of the present invention and a salt thereof are referred to as the "trisazo compound of the present invention".

Formula (6):

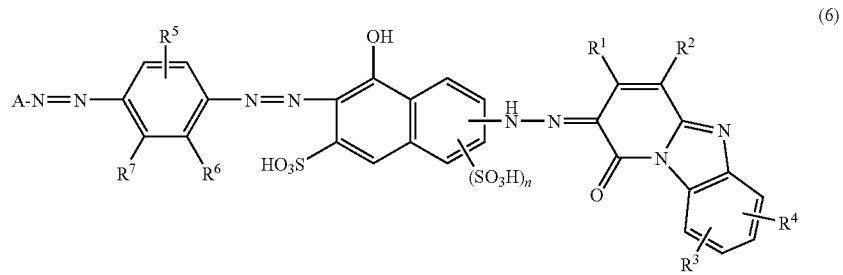

(Wherein, n, the group A and $R^1$ to $R^7$ have the same meanings as in the formula (1).)

Formula (7):

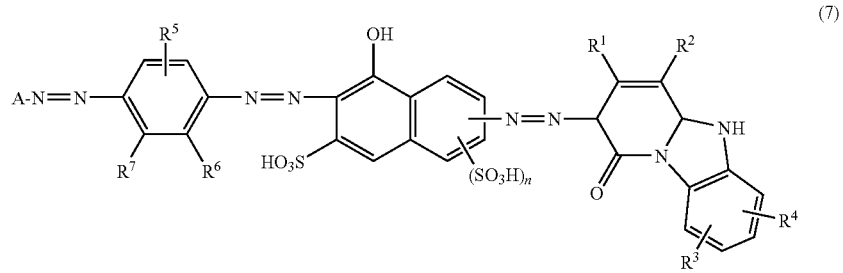

(Wherein, n, the group A and $R^1$ to $R^7$ have the same meanings as in the formula (1).)

Formula (8):

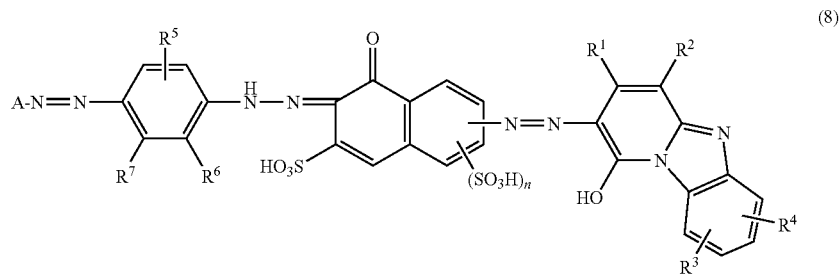

(Wherein, n, the group A and $R^1$ to $R^7$ have the same meanings as in the formula (1).)

Formula (9):

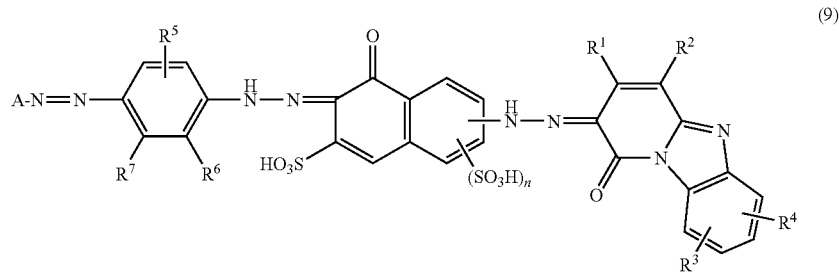

(Wherein, n, the group A and $R^1$ to $R^7$ have the same meanings as in the formula (1).)

Formula (10):

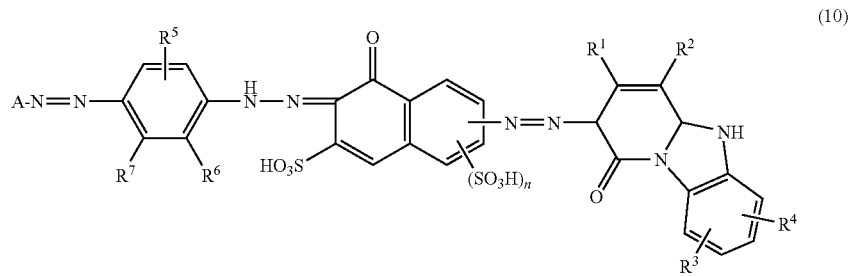

(Wherein, n, the group A and $R^1$ to $R^7$ have the same meanings as in the formula (1).)

In the above formula (1), formula (4) and formula (5), $R^1$ represents a carboxy group; an unsubstituted C1-C4 alkyl group; a C1-C4 alkyl group substituted by a carboxy group; an unsubstituted phenyl group; or a phenyl group substituted by a sulfo group.

The unsubstituted C1-C4 alkyl group for $R^1$ may be any of straight-chain and branched-chain, and preferably straight-chain. Specific examples of the C1-C4 alkyl group include, for example, straight-chain ones such as methyl, ethyl, n-propyl and n-butyl, and branched-chain ones such as isopropyl, isobutyl, sec-butyl and tert-butyl. Among them, a methyl group is more preferable.

The C1-C4 alkyl group substituted by a carboxy group for $R^1$ can include ones having a carboxy substitution on the above unsubstituted C1-C4 alkyl group. The substitution position of the carboxy group is not particularly limited, but it is preferably on the terminal of the alkyl chain. Specific examples thereof include carboxymethyl, 2-carboxyethyl and 3-carboxypropyl.

Specific examples of the phenyl group substituted by a sulfo group for $R^1$ include, for example, a phenyl group substituted by 1 to 2 sulfo groups such as 2-sulfophenyl, 4-sulfophenyl, 2,4-disulfophenyl and 3,5-disulfophenyl.

As $R^1$, among the above, an unsubstituted C1-C4 alkyl group and an unsubstituted phenyl group are preferable and an unsubstituted C1-C4 alkyl group is further preferable.

Specific examples of $R^1$ in the formula (1) are preferably methyl, ethyl, n-propyl, tert-butyl and phenyl, more preferably methyl, n-propyl and phenyl, and further preferably methyl and n-propyl. A methyl group is most preferable.

$R^2$ in the above formula (1), formula (4) and formula (5) represents a cyano group; a carbamoyl group; or a carboxy group, preferably cyano or carbamoyl, and further preferably cyano.

A preferable combination of $R^1$ and $R^2$ is a combination where $R^1$ is methyl and $R^2$ is cyano or a combination where $R^1$ is methyl and $R^2$ is carbamoyl. The former combination is more preferable.

In the above formula (1), formula (4) and formula (5), $R^3$ and $R^4$ each independently represent a hydrogen atom; a chlorine atom; a sulfo group; an unsubstituted C1-C4 alkyl group; or an unsubstituted C1-C4 alkoxy group; respectively.

The unsubstituted C1-C4 alkyl group for $R^3$ and $R^4$ is the same as the unsubstituted C1-C4 alkyl group for the above $R^1$.

The unsubstituted C1-C4 alkoxy group for $R^3$ and $R^4$ is preferably any of straight-chain or branched-chain, and specific examples thereof include methoxy, ethoxy, n-propoxy, isopropoxy, n-butoxy, sec-butoxy and tert-butoxy.

$R^3$ and $R^4$ are, preferably among the above, each independently a hydrogen atom; a sulfo group; or an unsubstituted C1-C4 alkyl group.

Preferable specific examples of $R^3$ and $R^4$ are each independently a hydrogen atom, sulfo, methyl, ethyl, n-propyl, isopropyl or tert-butyl, more preferably a hydrogen atom, sulfo, methyl or isopropyl, and further preferably a hydrogen atom or sulfo.

A preferable combination of $R^3$ and $R^4$ is a combination where one is a sulfo group and the other is a hydrogen atom.

In the above formula (1) and formula (4), $R^5$ to $R^7$ each independently represent a hydrogen atom; a chlorine atom; a hydroxy group; a sulfo group; a carboxy group; a sulfamoyl group; a carbamoyl group; an unsubstituted C1-C4 alkyl group; an unsubstituted C1-C4 alkoxy group; a C1-C4 alkoxy group substituted by a hydroxy group, an unsubstituted C1-C4 alkoxy group, a hydroxy C1-C4 alkoxy group, sulfo group or a carboxy group; a mono- or di-unsubstituted C1-C4 alkylamino group; a mono- or di-C1-C4 alkylamino group substituted by a hydroxy group, a sulfo group or a carboxy group; an unsubstituted C1-C4 alkylcarbonylamino group; a C1-C4 alkylcarbonylamino group substituted by a hydroxy group or a carboxy group; an unsubstituted N'-C1-C4 alkylureide group; an N'-C1-C4 alkylureide group substituted by a hydroxy group, a sulfo group or a carboxy group; an unsubstituted phenylamino group; a phenylamino group where the benzene ring is substituted by a chlorine atom, an unsubstituted C1-C4 alkyl group, a nitro group, a sulfo group or a carboxy group; an unsubstituted benzoylamino group; a benzoylamino group where the benzene ring is substituted by a chlorine atom, an unsubstituted C1-C4 alkyl group, a nitro group, a sulfo group or a carboxy group; an unsubstituted phenylsulfonylamino group; or a phenylsulfonylamino group where the benzene ring is substituted by a chlorine atom, an unsubstituted C1-C4 alkyl group, a nitro group, a sulfo group or a carboxy group; respectively.

Among the above, preferable as $R^5$ is a sulfo group; an unsubstituted C1-C4 alkoxy group; a C1-C4 alkoxy group substituted by a hydroxy group, a hydroxy C1-C4 alkoxy group, a sulfo group or a carboxy group; a di-C1-C4 alkylamino group substituted by a hydroxy group, a sulfo group or a carboxy group; an unsubstituted C1-C4 alkylcarbonylamino group; or a C1-C4 alkylcarbonylamino group substituted by a hydroxy group or a carboxy group, and more preferable is a C1-C4 alkoxy group substituted by a sulfo group. The C1-C4 alkoxy group substituted by a sulfo group is more preferably a C2-C4 alkoxy group substituted by a sulfo group and most preferably a sulfopropoxy group.

Among the above, $R^6$ is particularly preferably a hydrogen atom.

Among the above, preferable as $R^7$ is an unsubstituted C1-C4 alkyl group; an unsubstituted C1-C4 alkoxy group; a C1-C4 alkoxy group substituted by a hydroxy group; an unsubstituted C1-C4 alkylcarbonylamino group; an N'-C1-C4 alkylureide group substituted by a sulfo group or a carboxy group, and more preferable is an unsubstituted C1-C4 alkyl group. The unsubstituted C1-C4 alkyl group is more preferably a methyl group.

The unsubstituted C1-C4 alkyl group for the above $R^5$ to $R^7$ is the same as the unsubstituted C1-C4 alkyl group for $R^1$ described above. It is preferably a straight-chain C1-C4 alkyl group and can include, for example, methyl, ethyl, n-propyl, n-butyl and the like, and methyl or ethyl are more preferable.

The unsubstituted C1-C4 alkoxy group for $R^5$ to $R^7$ is the same as the unsubstituted C1-C4 alkoxy group for $R^3$ and $R^4$.

The substituted C1-C4 alkoxy group for $R^5$ to $R^7$, namely an alkoxy group substituted by a hydroxy group, an unsubstituted C1-C4 alkoxy group, a hydroxy C1-C4 alkoxy group, a sulfo group or a carboxy group includes, for example, a hydroxy C1-C4 alkoxy group such as 2-hydroxyethoxy, 2-hydroxypropoxy and 3-hydroxypropoxy; an unsubstituted C1-C4 alkoxy C1-C4 alkoxy group such as methoxyethoxy, ethoxyethoxy, n-propoxyethoxy, isopropoxyethoxy, n-butoxyethoxy, methoxypropoxy, ethoxypropoxy, n-propoxypropoxy, isopropoxybutoxy and n-propoxybutoxy; a hydroxy C1-C4 alkoxy C1-C4 alkoxy group such as 2-hydroxyethoxyethoxy; a sulfo C1-C4 alkoxy group such as 3-sulfopropoxy and 4-sulfobutoxy; a carboxy C1-C4 alkoxy group such as carboxymethoxy, 2-carboxyethoxy and 3-carboxypropoxy; and the like.

The unsubstituted mono- or di-C1-C4 alkylamino group for $R^5$ to $R^7$ include ones where the alkyl moiety is straight-chain such as methylamino, ethylamino, n-propylamino, n-butylamino, dimethylamino, diethylamino, di-n-propylamino and di-n-butylamino, ones where the alkyl moiety is branched-chain such as isopropylamino, sec-butylamino, tert-butylamino and diisopropylamino, and the like.

The mono- or di-C1-C4 alkylamino group substituted by a hydroxy group, a sulfo group or a carboxy group for $R^5$ to $R^7$ include, for example, a mono or di(hydroxy substituted C1-C4 alkyl)amino group such as 2-hydroxyethylamino, 2-hydroxypropylamino and 2,2'-dihydroxydiethylamino; a mono or di(sulfo-substituted C1-C4 alkyl)amino group such as 2-sulfoethylamino, 3-sulfopropylamino, 4-sulfobutylamino and 3,3'-disulfodipropylamino; and a mono- or di(carboxy-substituted C1-C4 alkyl)amino group such as carboxymethylamino, 2-carboxyethylamino, 3-carboxypropylamino and 2,2'-di-carboxydiethylamino.

The unsubstituted C1-C4 alkylcarbonylamino group for $R^5$ to $R^7$ may be one where said C1-C4 alkyl moiety is any of straight-chain or branched-chain and preferably straight-chain. Specific examples thereof include acetylamino, propanoylamino, butanoylamino and pentanoylamino.

The C1-C4 alkylcarbonylamino group substituted by a hydroxy group or a carboxy group for $R^5$ to $R^7$ includes, for example, a hydroxy C1-C4 alkylcarbonylamino group such as hydroxyethanoylamino, 2-hydroxy propanoylamino and 4-hydroxybutanoylamino; and a carboxy C1-C4 alkylcarbonylamino group such as 3-carboxypropanoylamino.

The N'-C1-C4 alkylureide group for $R^5$ to $R^7$ is more preferably one having a substituent than an unsubstituted one. The N'-C1-C4 alkylureide group having a hydroxy group, a sulfo group or a carboxy group as a substituent includes, for example, an N'-hydroxy C1-C4 alkylureide group such as N'-2-hydroxyethylureide and N'-3-hydroxypropylureide; an N'-sulfo C1-C4 alkylureide group such as N'-2-sulfoethylureide and N'-3-sulfopropyl ureide; and an N'-carboxy C1-C4 alkylureide group such as N'-carboxymethylureide, N'-2-carboxyethylureide, N'-3-carboxypropyl ureide and N'-4-carboxybutyl ureide.

The phenylamino, benzoylamino or phenylsulfonylamino group having an unsubstituted C1-C4 alkyl group on the benzene ring for $R^5$ to $R^7$ can include those groups having an unsubstituted C1-C4 alkyl group which is straight-chain, branched-chain or cyclic (in the case of C3 or C4), and those groups having a straight-chain or branched-chain unsubstituted C1-C4 alkyl group are preferable. Said unsubstituted C1-C4 alkyl group includes, for example, straight-chain alkyl such as methyl, ethyl, n-propyl and n-butyl; and branched-chain alkyl such as isopropyl, isobutyl, sec-butyl and tert-butyl.

The phenylamino group where the benzene ring is substituted by a chlorine atom, an unsubstituted C1-C4 alkyl group, a nitro group, a sulfo group or a carboxy group for $R^5$ to $R^7$ include, for example, a chlorine atom-substituted phenylamino group such as 2-chlorophenylamino, 4-chlorophenylamino and 2,4-dichlorophenylamino; a C1-C4 alkyl-substituted phenylamino group such as 2-methylphenylamino, 4-methylphenylamino and 4-tert-butylphenylamino; a nitro-substituted phenylamino group such as 2-nitrophenylamino and 4-nitrophenylamino; a sulfo-substituted phenylamino group such as 3-sulfophenylamino, 4-sulfophenylamino, 2,4-disulfophenylamino and 3,5-disulfophenylamino; and a carboxy-substituted phenylamino group such as 2-carboxyphenylamino, 4-carboxyphenylamino, 2,5-dicarboxyphenylamino and 3,5-dicarboxyphenylamino.

The benzoylamino group where the benzene ring is substituted by a chlorine atom, a C1-C4 alkyl group, a nitro group, a sulfo group or a carboxy group for $R^5$ to $R^7$ includes, for example, a chlorine atom-substituted benzoylamino group such as 2-chlorobenzoylamino, 4-chlorobenzoylamino and 2,4-dichlorobenzoylamino; a C1-C4 alkyl-substituted benzoylamino group such as 2-methylbenzoylamino, 3-methylbenzoylamino and 4-methylbenzoylamino; a nitro-substituted benzoylamino group such as 2-nitrobenzoylamino, 4-nitrobenzoylamino and 3,5-dinitrobenzoylamino; a sulfo-substituted benzoylamino group such as 2-sulfobenzoylamino and 4-sulfobenzoylamino; a carboxy-substituted benzoylamino group such as 2-carboxybenzoylamino, 4-carboxybenzoylamino and 3,5-dicarboxybenzoylamino.

Specific examples of the phenylsulfonylamino group where the benzene ring is substituted by a chlorine atom, a C1-C4 alkyl group, a nitro group, a sulfo group or a carboxy group for $R^5$ to $R^7$ includes, for example, a chlorine atom-substituted phenylsulfonylamino group such as 2-chlorophenylsulfonylamino and 4-chlorophenylsulfonylamino; a C1-C4 alkyl-substituted phenylsulfonylamino group such as 2-methylphenylsulfonylamino, 4-methylphenylsulfonylamino and 4-tert-butylphenylsulfonylamino; a nitro-substituted phenylsulfonylamino group such as 2-nitrophenylsulfonylamino, 3-nitrophenylsulfonylamino and 4-nitrophenylsulfonylamino; a sulfo-substituted phenylsulfonylamino group such as 3-sulfophenylsulfonylamino and 4-sulfophenylsulfonylamino; a carboxy-substituted phenylsulfonylamino group such as 3-carboxyphenylsulfonylamino and 4-carboxyphenylsulfonylamino.

Preferable specific examples of $R^5$ to $R^7$ are each independently a hydrogen atom, carboxy, sulfo, methyl, ethyl, methoxy, ethoxy, 2-hydroxyethoxy, 2-sulfoethoxy, 3-sulfopropoxy, 4-sulfobutoxy, carboxymethoxy, 2-carboxyethoxy, methylamino, ethylamino, 2-hydroxyethylamino, 2-sulfoethylamino, 3-sulfopropylamino, 2-carboxyethylamino, dimethylamino, diethylamino, 2,2'-dihydroxydiethylamino, 2,2'-dicarboxydiethylamino, 3,3'-disulfodipropylamino, acetylamino, 3-carboxypropanoylamino, 4-hydroxybutanoylamino, N'-carboxymethylureide, N'-2-sulfoethylureide, 4-sulfophenylamino, 2,4-disulfophenylamino, 2,5-dicarboxyphenylamino, benzoylamino, 3-sulfobenzoylamino, 2-carboxybenzoylamino, phenylsulfonylamino, 4-methylphenyl-sulfonylamino, 4-nitrophenylsulfonylamino, 3-sulfophenylsulfonylamino and 4-carboxyphenylsulfonylamino. More preferable are a hydrogen atom, sulfo, methyl, methoxy, 2-hydroxyethoxy, 2-sulfoethoxy, 3-sulfopropoxy, 4-sulfobutoxy, dimethylamino, 3,3'-disulfodipropylamino, acetylamino, 3-carboxypropanoylamino, N'-2-sulfoethylureide, 2,4-disulfophenylamino, benzoylamino and 4-methylphenylsulfonylamino, and further preferable is a hydrogen atom, sulfo, methyl, methoxy or 3-sulfopropoxy.

A preferable combination of $R^5$ to $R^7$ in the formula (1) and the formula (4) is a combination where $R^5$ is any of the above preferable groups included as $R^5$, $R^6$ is a hydrogen atom, and $R^7$ is any of the above preferable groups included as $R^7$. A more preferable combination of $R^5$ to $R^7$ is a combination where $R^5$ is a sulfo-substituted C1-C4 alkoxy group, $R^6$ is a hydrogen atom, and $R^7$ is an unsubstituted C1-C4 alkyl group, and further preferably is a combination where $R^5$ is 3-sulfopropoxy or 4-sulfobutoxy, $R^6$ is a hydrogen atom and $R^7$ is methyl.

A more preferable combination of $R^{55}$ and $R^{77}$ in the formula (5) is a combination where $R^{55}$ is a 3-sulfopropoxy group and $R^{77}$ is methyl.

In the above formula (2), $R^8$ represents a mercapto group; an unsubstituted C1-C4 alkylthio group; or a C1-C4 alkylthio group substituted by a hydroxy group, an unsubstituted C1-C4 alkoxy group, a hydroxy C1-C4 alkoxy group, a sulfo group or a carboxy group.

When $R^8$ is an unsubstituted C1-C4 alkylthio group, said C1-C4 alkyl moiety is preferably any of straight-chain or branched-chain, and more preferably straight-chain. Specific examples thereof include methylthio, ethylthio, n-propylthio, isopropylthio, n-butylthio, sec-butylthio and tert-butylthio.

When $R^8$ is a C1-C4 alkylthio group having a substituent, said substituent is preferably a hydroxy group, a sulfo group or a carboxy group, and more preferably a sulfo group or a carboxy group. Specific examples of the C1-C4 alkylthio group having a substituent include, for example, a hydroxy C1-C4 alkylthio group such as 2-hydroxyethylthio, 2-hydroxypropylthio and 3-hydroxypropylthio; a C1-C4 alkoxy C1-C4 alkylthio group such as methoxyethylthio, ethoxyethylthio, n-propoxyethylthio, isopropoxyethylthio, n-butoxyethylthio, methoxypropylthio, ethoxypropylthio, n-propoxypropylthio, isopropoxybutylthio and n-propoxybutylthio; a hydroxy C1-C4 alkoxy C1-C4 alkylthio group such as 2-hydroxyethoxyethylthio; a sulfo C1-C4 alkylthio group such as 2-sulfoethylthio, 3-sulfopropylthio and 4-sulfobutylthio; a carboxy C1-C4 alkylthio group such as carboxymethylthio, 2-carboxyethylthio and 3-carboxypropylthio.

$R^8$ is preferably a hydroxy group, an unsubstituted C1-C4 alkoxy group, a hydroxy C1-C4 alkoxy group, and a C1-C4 alkylthio group substituted by a sulfo group or a carboxy group. More preferable is a C1-C4 alkylthio group substituted by a sulfo group or a carboxy group, and particularly preferable is a C1-C4 alkylthio group substituted by a sulfo group.

Preferable specific examples of $R^8$ are mercapto (—SH), methylthio, ethylthio, 2-hydroxyethylthio, methoxyethylthio, ethoxyethylthio, 2-sulfoethylthio, 3-sulfopropylthio, 4-sulfobutylthio, carboxymethylthio, 2-carboxyethylthio and 3-carboxypropylthio, and more preferable are methylthio, 2-sulfoethylthio, carboxymethylthio and 2-carboxyethylthio. Further preferable are 2-sulfoethylthio and 2-carboxyethylthio, and particularly preferable is 2-sulfoethylthio.

In the above formula (3), $R^9$ to $R^{11}$ each independently represent a hydrogen atom; a chlorine atom; a carboxy group; a sulfo group; a nitro group; a hydroxy group; a carbamoyl group; a sulfamoyl group; an unsubstituted C1-C4 alkyl group; an unsubstituted C1-C4 alkoxy group; a C1-C4 alkoxy group substituted by a hydroxy group, an unsubstituted C1-C4 alkoxy group, a sulfo group or a carboxy group; an unsubstituted C1-C4 alkylsulfonyl group; a C1-C4 alkylsulfonyl group substituted by a hydroxy group, a sulfo group or a carboxy group; an unsubstituted phenylsulfonyl group; or a phenylsulfonyl group where the benzene ring is substituted by a chlorine atom, an unsubstituted C1-C4 alkyl group, a nitro group, a sulfo group or a carboxy group. Among them, $R^9$ to $R^{11}$ are, preferably, each independently a hydrogen atom, a chlorine atom, a carboxy group, a sulfo group, a nitro group, an unsubstituted C1-C4 alkyl group, an unsubstituted C1-C4 alkoxy group or an unsubstituted C1-C4 alkylsulfonyl group.

At least any one of $R^9$ to $R^{11}$ is preferably one of the above groups other than a hydrogen atom. More preferably, at least any one of the above groups other than said hydrogen atom is a sulfo group or a carboxy group, and further preferably a sulfo group. In these cases, further, at least one of $R^9$ to $R^{11}$ is preferably a hydrogen atom. More preferably, one of $R^9$ to $R^{11}$ is a sulfo group, one of the rest is a hydrogen atom, and the other is one of the above groups other than a hydrogen atom. In addition, in this case, the other group other than a hydrogen atom is more preferably a chlorine atom, a carboxy group, a sulfo group, a nitro group, an unsubstituted C1-C4 alkyl group, an unsubstituted C1-C4 alkoxy group or an unsubstituted C1-C4 alkylsulfonyl group, and further preferably a chlorine atom, a sulfo group, a nitro group, an unsubstituted C1-C4 alkoxy group or an unsubstituted C1-C4 alkylsulfonyl group. Most preferably, the other group other than a hydrogen atom is a sulfo group or an unsubstituted C1-C4 alkoxy group.

The unsubstituted C1-C4 alkyl group for $R^9$ to $R^{11}$ may be any of straight-chain, branched-chain or cyclic (in the case of C3 or C4), preferably straight-chain or branched-chain and further preferably straight-chain. Specific examples thereof include, for example, straight-chain ones such as methyl, ethyl, n-propyl and n-butyl; and branched-chain ones such as isopropyl, isobutyl, sec-butyl and tert-butyl.

The unsubstituted C1-C4 alkoxy group for $R^9$ to $R^{11}$ can include a straight-chain or branched-chain C1-C4 alkoxy group such as methoxy, ethoxy, n-propoxy, isopropoxy, n-butoxy, sec-butoxy and tert-butoxy, and it is preferably straight-chain. As the straight-chain C1-C4 alkoxy group, a methoxy group is more preferable.

The C1-C4 alkoxy group substituted by a hydroxy group, an unsubstituted C1-C4 alkoxy group, a sulfo group or a carboxy group for $R^9$ to $R^{11}$ can include a C1-C4 alkoxy group having, as a substituent, a hydroxy group, an unsubstituted C1-C4 alkoxy group, a sulfo group or a carboxy group on the above unsubstituted C1-C4 alkoxy group. Specific examples, preferable groups and the like thereof are the same as those described above for $R^5$ to $R^7$ (see the paragraph 0048).

The unsubstituted C1-C4 alkylsulfonyl group, or the C1-C4 alkylsulfonyl group substituted by a hydroxy group, a sulfo group or a carboxy group for $R^9$ to $R^{11}$ include, for example, an straight-chain or branched-chain unsubstituted C1-C4 alkylsulfonyl group such as methylsulfonyl, ethylsulfonyl, propylsulfonyl, isopropylsulfonyl, n-butylsulfonyl, sec-butylsulfonyl and tert-butylsulfonyl; a hydroxy C1-C4 alkylsulfonyl group such as 2-hydroxyethylsulfonyl and 3-hydroxypropylsulfonyl; a sulfo C1-C4 alkylsulfonyl group such as 2-sulfopropylsulfonyl, 3-sulfopropylsulfonyl and 4-sulfo butylsulfonyl; a carboxy C1-C4 alkylsulfonyl group such as carboxymethylsulfonyl, 2-carboxyethylsulfonyl, 3-carboxypropylsulfonyl.

Specific examples of the unsubstituted phenylsulfonyl group; or the phenylsulfonyl group where the benzene ring is substituted by a chlorine atom, an unsubstituted C1-C4 alkyl group, a nitro group, a sulfo group or a carboxy group for $R^9$ to $R^{11}$ include, for example, unsubstituted phenylsulfonyl; a chlorine atom-substituted phenylsulfonyl group such as 2-chlorophenylsulfonyl and 4-chlorophenylsulfonyl; a C1-C4 alkyl-substituted phenylsulfonyl group such as 2-methylphenylsulfonyl, 4-methylphenylsulfonyl, 2,4-dimethylphenylsulfonyl and 4-tert-butylphenylsulfonyl; a nitro-substituted phenylsulfonyl group such as 2-nitrophenylsulfonyl and 4-nitrophenylsulfonyl; a sulfo-substituted phenylsulfonyl group such as 3-sulfophenylsulfonyl, 4-sulfophenylsulfonyl and 3,5-disulfophenylsulfonyl; a carboxy-substituted phenylsulfonyl group such as 2-carboxyphenylsulfonyl, 4-carboxyphenylsulfonyl and 3,5-dicarboxyphenylsulfonyl.

Preferable specific examples of $R^9$ to $R^{11}$ each independently can include a hydrogen atom, a chlorine atom, carboxy, sulfo, nitro, methyl, ethyl, methoxy, ethoxy, 2-hydroxyethoxy, 2-sulfoethoxy, 3-sulfopropoxy, 4-sulfobutoxy, carboxymethoxy, 2-carboxyethoxy, methylsulfonyl, ethylsulfonyl, tert-butylsulfonyl, 2-hydroxyethylsulfonyl, 3-sulfopropylsulfonyl, 2-carboxyethylsulfonyl, phenylsulfonyl, 4-chlorophenylsulfonyl, 4-methylphenylsulfonyl, 2,4-dimethylphenylsulfonyl, 4-nitrophenylsulfonyl, 4-sulfophenylsulfonyl, 2-carboxyphenylsulfonyl or 4-carboxyphenylsulfonyl. More preferable specific examples can likewise include a hydrogen atom, a chlorine atom, carboxy, sulfo, nitro, methyl, methoxy, methylsulfonyl or 2-carboxyphenylsulfonyl. Further preferable specific examples thereof can likewise include a hydrogen atom, a chlorine atom, carboxy, sulfo, nitro, methyl, methoxy or methylsulfonyl, and particularly preferable specific examples thereof are likewise a hydrogen atom, a chlorine atom, sulfo and methoxy.

At least one of $R^9$ to $R^{11}$ is preferably a hydrogen atom, and also at least one of the rest groups is preferably a group included in the above specific examples other than a hydrogen atom. In this case, the group included in the above specific examples other than a hydrogen atom is more preferably a group described in the more preferable specific examples, the further preferable specific examples and the particularly preferable specific examples, other than a hydrogen atom. Particularly, it is preferable that one of $R^9$ to $R^{11}$ is a hydrogen atom, and the rest two are each independently a group described in the more preferable specific examples, the further preferable specific examples and the particularly preferable specific examples described above, other than a hydrogen atom.

$R^9$ is preferably a hydrogen atom, a chlorine atom or a sulfo group.

$R^{10}$ is preferably a chlorine atom, a carboxy group, a sulfo group, nitro, an unsubstituted C1-C4 alkyl group, an unsubstituted C1-C4 alkoxy group or an unsubstituted C1-C4 alkylsulfonyl group, and more preferably a chlorine atom, carboxy, sulfo, nitro, methyl, methoxy or methylsulfonyl.

$R^{11}$ is preferably a hydrogen atom or a sulfo group.

Compounds of the formula (1), the formula (4) or the formula (5) having these preferable $R^9$ to $R^{11}$ are preferable. In addition, when $R^{10}$ is one of the above more preferable groups, said compounds are further preferable. In these combinations, it is further preferable that at least one of $R^9$ or $R^{11}$ is a hydrogen atom, at least one of the rest groups and preferably at least one of $R^9$ or $R^{11}$ is a sulfo group.

The substitution positions of $R^9$ to $R^{11}$ on the benzothiazole ring are not particularly limited and may be any three of the 4 to 7 positions, and when two of $R^9$ to $R^{11}$ are substituents other than a hydrogen atom, the preferable substitution positions are the 4-position and the 6-position, the 5-position and the 6-position, or the 6-position and the 7-position; and when one of them is a substituent other than a hydrogen atom, the preferable position is the 6-position. For example, specifically, a compound where $R^9$ is at the 4-position or the 5-position, $R^{10}$ is at the 6-position and $R^{11}$ is at the 7-position can be included.

Preferable combinations of $R^9$ to $R^{11}$ in the formula (3) include a combination where any one of them is a hydrogen atom, either of the rest is a methoxy group and the other is a sulfo group; a combination where any one of them is a hydrogen atom, either of the rest is a chlorine atom and the other is a sulfo group; and a combination where two of them are sulfo groups and the rest one is a hydrogen atom. In the combination where two of them are sulfo groups and the rest is a hydrogen atom, the substitution positions of the sulfo groups are more preferably the 4-position and the 6-position of the benzothiazole ring.

In the formula (1), the formulas (4) and (5), n is preferably 1.

In addition, in the formula (1), the azo group to be bonded to the benzimidazolopyridone ring is preferably bonded at b-position of the naphthalene ring, and further, said naphthalene ring is preferably substituted at c-position by a sulfo group represented by —$(SO_3H)n$ on.

A compound containing a combination of the preferable groups described for the substituents in the above formulas (1) to (3) is more preferable, and a compound containing a combination of more preferable groups is further preferable. The same goes for a combination of the further preferable groups.

One of the preferable compounds represented by the above formula (1) can include a compound represented by the formula (4), and further preferable compounds can include a compound of the formula (5). In addition, as for these compounds of the formula (1), the formula (4) and the formula (5), more preferable compounds include a compound having the above preferable combination of $R^1$ and $R^2$ and the above preferable combination of $R^3$ and $R^4$, where $R^8$ is any of the above preferable groups included as $R^8$ when the group A is represented by the formula (2) or where the combination of $R^9$ to $R^{11}$ is the above preferable one (more preferably the above more preferable combination of $R^9$ to $R^{11}$ and further preferably the above further preferable combination of $R^9$ to $R^{11}$) when the group A is represented by the formula (3). Further, in the formula (1) and the formula (4), for the above "more preferable compound", a compound having the above preferable combination of $R^5$ to $R^7$ (more preferably the above more preferable combination of $R^5$ to $R^7$ and further preferably the above further preferable combination of $R^5$ to $R^7$) is further preferable.

Furthermore, in any of the above compounds (the compound of the formula (1), the formula (4) and the formula (5), their more preferable compounds and further preferable compounds), n is more preferably 1. Moreover, in the above, when n of the compound of the formula (1) is 1, further preferable is a compound where the azo group to be bonded to the benzimidazolopyridone ring is bonded at b-position of the naphthalene ring and also said naphthalene ring is substituted at c by a sulfo group represented by —$(SO_3H)n$.

One of the preferable compounds represented by the above formula (1), formula (4) and formula (5) can include, for example, compounds where the group A is a substituted heterocyclic group represented by the formula (2) or the formula (3), $R^8$ of the formula (2) is a sulfo C1-C4 alkylthio group or a carboxy C1-C4 alkylthio group, $R^9$ to $R^{11}$ of the formula (3) are each independently a hydrogen atom, a chlorine atom, a carboxy group, a sulfo group, a nitro group, an unsubstituted C1-C4 alkyl group, an unsubstituted C1-C4 alkoxy group or an unsubstituted C1-C4 alkylsulfonyl group, $R^1$ is a methyl group, $R^2$ is a cyano group or a carbamoyl group, $R^3$ is a hydrogen atom and $R^4$ is a sulfo group. In these preferable compounds, n is more preferably 1. In addition, in these preferable compounds and more preferable compounds of the formulas (1) and (4), it is further preferable that $R^5$ to $R^7$ are, further, each independently a hydrogen atom; an unsubstituted C1-C4 alkyl group; an unsubstituted C1-C4 alkoxy group; a C1-C4 alkoxy group substituted by hydroxy group or a sulfo group; a dialkylamino group substituted by a carboxy group, a sulfo group or a hydroxy group; an unsubstituted C1-C4 alkylcarbonylamino group; an N'-C1-C4 alkylureide group substituted by a sulfo group or a carboxy group; or an unsubstituted benzoylamino group. Furthermore, in these compounds, any one of $R^5$ to $R^7$ is further preferably a C1-C4 alkoxy group substituted by a sulfo group. Most preferably, $R^5$ to $R^7$ are each independently a hydrogen atom; an unsubstituted C1-C4 alkyl group; and a C1-C4 alkoxy group substituted by a sulfo group, and at least any one thereof is a C1-C4 alkoxy group substituted by a sulfo group.

In addition, preferable compounds of the above formula (1) or (4) can include a compound where $R^1$ is methyl, n-propyl or phenyl and more preferably methyl; $R^2$ is cyano or carbamoyl and more preferably cyano; $R^3$ is a hydrogen atom and $R^4$ is a sulfo group, or $R^3$ is a sulfo group and $R^4$ is a hydrogen atom group; $R^5$ is a sulfo-substituted C1-C4 alkoxy group and more preferably 3-sulfopropoxy; $R^6$ is a hydrogen atom; $R^7$ is an unsubstituted C1-C4 alkyl group and more preferably methyl; when the group A is represented by the formula (2), $R^8$ is a sulfo-substituted C1-C4 alkylthio group and more preferably 2-sulfoethylthio; when the group A is represented by the formula (3), $R^9$ to $R^{11}$ are each independently a hydrogen atom, a chlorine atom, a carboxy group, a sulfo group, a nitro group, an unsubstituted C1-C4 alkyl group, an unsubstituted C1-C4 alkoxy group or an unsubstituted C1-C4 alkylsulfonyl group and more preferably a hydrogen atom, a chlorine atom, carboxy, sulfo, nitro, methyl, methoxy or methylsulfonyl, and further preferable is a combination where $R^9$ is a hydrogen atom, a chlorine atom or a sulfo group, $R^{10}$ is a chlorine atom, carboxy, sulfo, nitro, methyl, methoxy or methylsulfonyl, $R^{11}$ is a hydrogen atom or a sulfo group, and at least one of $R^9$ to $R^{11}$ is a sulfo group or a carboxy group; n is a 1; the bonding position of the azo group to be bonded to benzimidazolopyridone ring is b of the naphthalene ring; and said naphthalene ring is substituted at c by a sulfo group represented by —$(SO_3H)n$.

Furthermore, n, the group A and $R^1$ to $R^7$ in the formulas (6) to (10) have the same meanings as in the formula (1), including the preferable groups, the combinations of preferable groups and the like.

The salts of the trisazo compounds represented by the above formula (1), formula (4) and formula (5) are inorganic or organic cation salts. Specific examples of the inorganic salt include alkali metal salt, alkali earth metal salt and ammonium salt, and the inorganic salts are preferably salts of lithium, sodium and potassium and ammonium salt; and the organic cation salt includes, for example, salts with quaternary ammonium ion represented by the following formula (11); but the both are not limited thereto. In addition, the salts may be free acid, tautomers thereof and a mixture of various salts thereof. For example, any combination may be used such as a mixture of sodium salt and ammonium salt, a mixture of free acid and sodium salt, a mixture of free acid and ammonium salt, and a mixture of lithium salt, sodium salt and ammonium salt. The physical property value such as solubility may vary depending on the kind of salt, and a mixture having intended physical properties can be obtained by appropriately selecting the kind of salt according to necessity and by changing the ratio of salts when a plurality of salts are composed.

Formula (11):

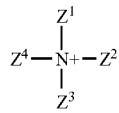

(11)

In the formula (11), $Z^1$, $Z^2$, $Z^3$ and $Z^4$ each independently represent a group selected from the group consisting of a hydrogen atom, an alkyl group, a hydroxyalkyl group and a hydroxyalkoxyalkyl group.

Specific examples of the alkyl group of $Z^1$, $Z^2$, $Z^3$ and $Z^4$ in the formula (11) include methyl, ethyl, n-propyl, isopropyl, n-butyl, isobutyl, sec-butyl, tert-butyl and the like; specific examples of the hydroxyalkyl group include a hydroxy C1-C4 alkyl group such as hydroxymethyl, hydroxyethyl, 3-hydroxypropyl, 2-hydroxypropyl, 4-hydroxybutyl, 3-hydroxybutyl and 2-hydroxybutyl; examples of the hydroxyalkoxyalkyl group include a hydroxy C1-C4 alkoxy C1-C4 alkyl group such as hydroxyethoxymethyl, 2-hydroxyethoxyethyl, 3-hydroxyethoxypropyl, 2-hydroxyethoxypropyl, 4-hydroxyethoxybutyl, 3-hydroxyethoxybutyl and 2-hydroxyethoxybutyl, and preferable among them is hydroxyethoxy C1-C4 alkyl. Particularly preferable ones include a hydrogen atom; a hydroxy C1-C4 alkyl group such as methyl, hydroxymethyl, hydroxyethyl, 3-hydroxypropyl, 2-hydroxypropyl, 4-hydroxybutyl, 3-hydroxybutyl and 2-hydroxybutyl; and a hydroxyethoxy C1-C4 alkyl group such as hydroxyethoxymethyl, 2-hydroxyethoxyethyl, 3-hydroxyethoxypropyl, 2-hydroxyethoxypropyl, 4-hydroxyethoxybutyl, 3-hydroxyethoxybutyl and 2-hydroxyethoxybutyl.

Specific combination examples of $Z^1$, $Z^2$, $Z^3$ and $Z^4$ of the preferable compounds in the formula (11) are shown in the table below.

TABLE 1

| Compound No. | Z1 | Z2 | Z3 | Z4 |
|---|---|---|---|---|
| 1-1 | H | CH3 | CH3 | CH3 |
| 1-2 | CH3 | CH3 | CH3 | CH3 |
| 1-3 | H | —C2H4OH | —C2H4OH | —C2H4OH |
| 1-4 | CH3 | —C2H4OH | —C2H4OH | —C2H4OH |
| 1-5 | H | —CH2CH(OH)CH3 | —CH2CH(OH)CH3 | —CH2CH(OH)CH3 |
| 1-6 | CH3 | —CH2CH(OH)CH3 | —CH2CH(OH)CH3 | —CH2CH(OH)CH3 |
| 1-7 | H | —C2H4OH | H | —C2H4OH |
| 1-8 | CH3 | —C2H4OH | H | —C2H4OH |
| 1-9 | H | —CH2CH(OH)CH3 | H | —CH2CH(OH)CH3 |
| 1-10 | CH3 | —CH2CH(OH)CH3 | H | —CH2CH(OH)CH3 |
| 1-11 | CH3 | —C2H4OH | CH3 | —C2H4OH |
| 1-12 | CH3 | —CH2CH(OH)CH3 | CH3 | —CH2CH(OH)CH3 |

The trisazo compound represented by the above formula (1) can be synthesized by, for example, the following method. In this regard, acidic functional groups of compounds in the processes are shown in free acid form, for convenience.

In addition, in the formulas (12) to (17) below, n, the group A and $R^1$ to $R^7$ have the same meanings as in the formula (1), respectively.

A compound represented by the following formula (12) is diazotized by a conventional method, and the resulting diazo compound and a compound represented by the following formula (13) are subjected to coupling reaction by a conventional method to obtain a compound represented by the following formula (14).

Formula (12), Formulas (13) and (14):

(12)

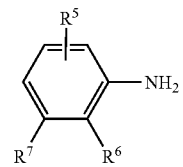

(13)

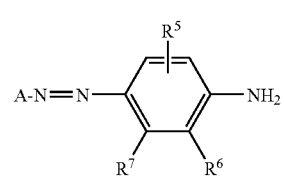

(14)

The obtained compound represented by the formula (14) is diazotized by a conventional method, and then the resulting diazo compound and a compound represented by the following formula (15) are subjected to coupling reaction by a conventional method to obtain a compound represented by the following formula (16).

Formula (15) and Formula (16):

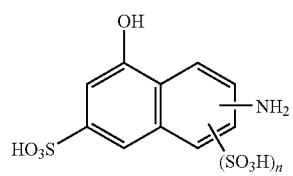

(15)

-continued (16)

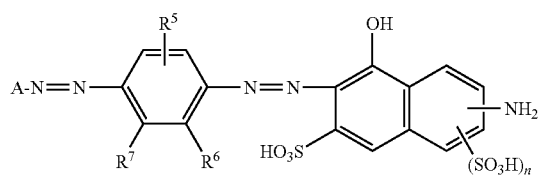

The obtained compound represented by the formula (16) is diazotized by a conventional method, and then the resulting diazo compound and a compound represented by the following formula (17) are subjected to coupling reaction by a conventional method to obtain the trisazo compound of the present invention represented by the above formula (1).

In addition, compounds of the formula (4) and the formula (5) can be obtained by using compounds corresponding to the formula (4) or the formula (5) respectively as compounds of the formula (13) and the formula (15) in the above synthesis method of the formula (1).

Formula (17):

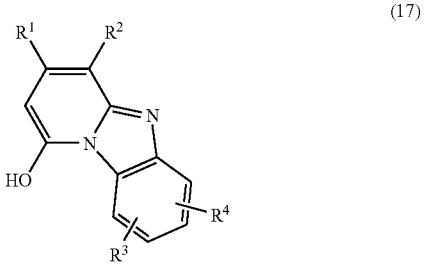

Furthermore, the compound represented by the above formula (17) can be synthesized in accordance with the method described in Patent Literature 5.

Suitable specific examples of the compound of the present invention shown by the above formula (1) are not particularly limited, but include the compounds shown by the structural formulas included in the following tables 2 to 17.

In the tables, acidic functional groups are depicted in free acid form, for convenience.

TABLE 2

| Comp. No. | Structural Formula |
|---|---|
| 1 | |
| 2 | |
| 3 | |

TABLE 2-continued

| Comp. No. | Structural Formula |
|---|---|
| 4 | |
| 5 | |
| 6 | |
| 7 | |

TABLE 3
| Comp. No. | Structural Formula |
|---|---|
| 8 | 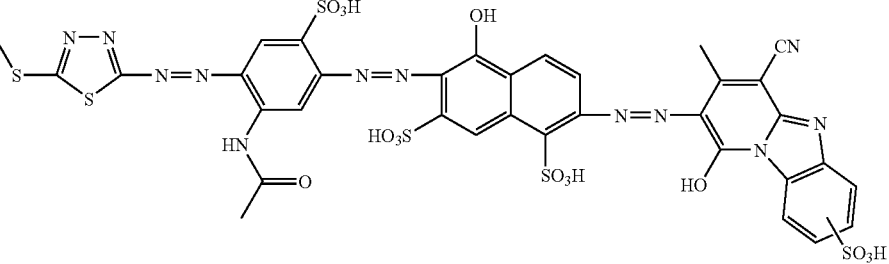 |
| 9 | 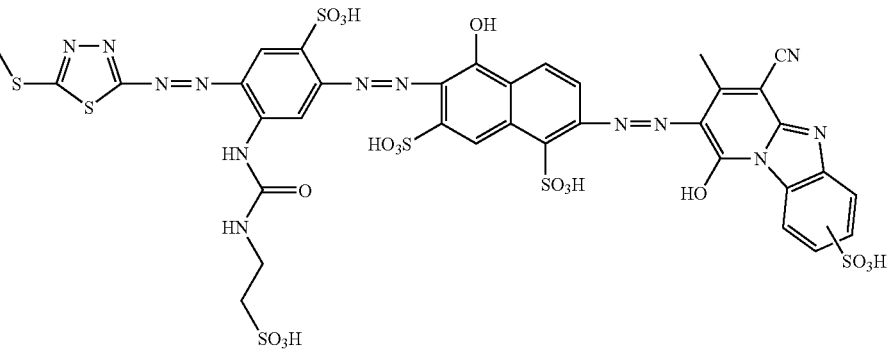 |
| 10 | 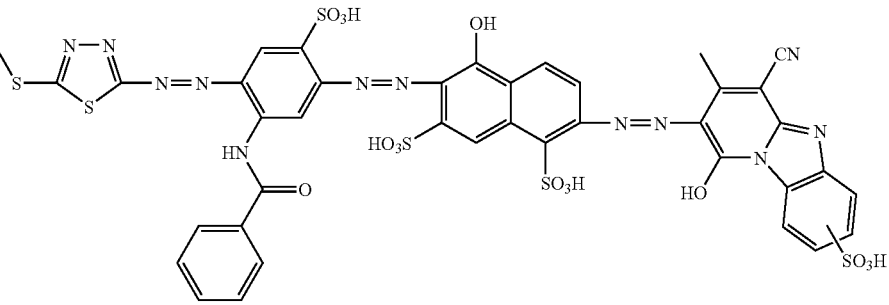 |
| 11 | 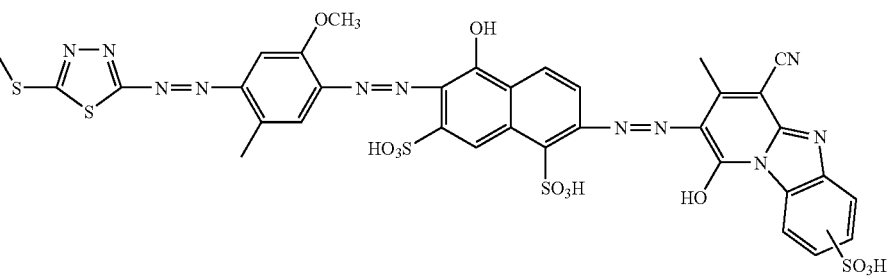 |
| 12 | 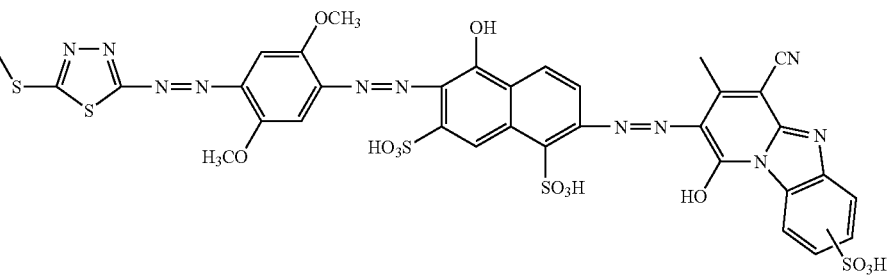 |

TABLE 3-continued
| Comp. No. | Structural Formula |
|---|---|
| 13 | 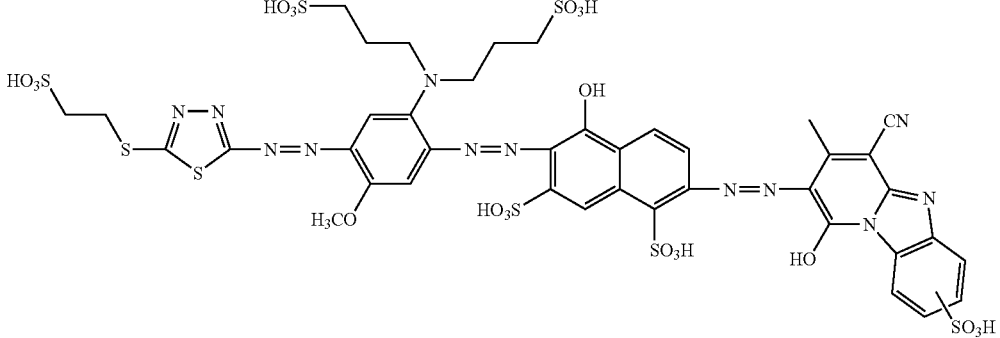 |
| 14 | 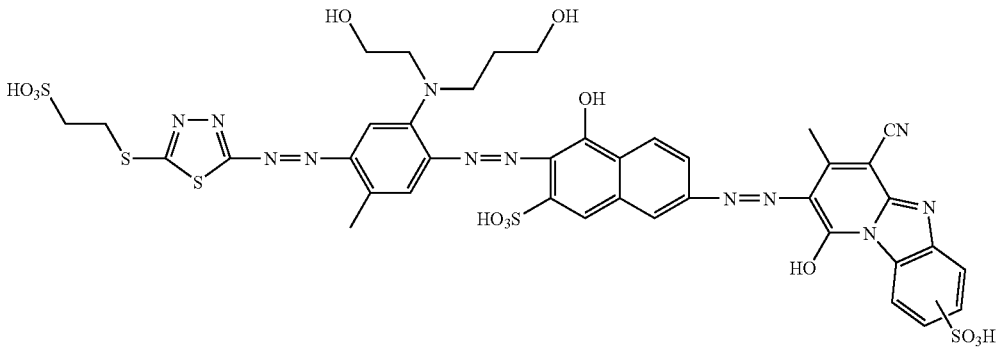 |
TABLE 4
| Comp. No. | Structural Formula |
|---|---|
| 15 | 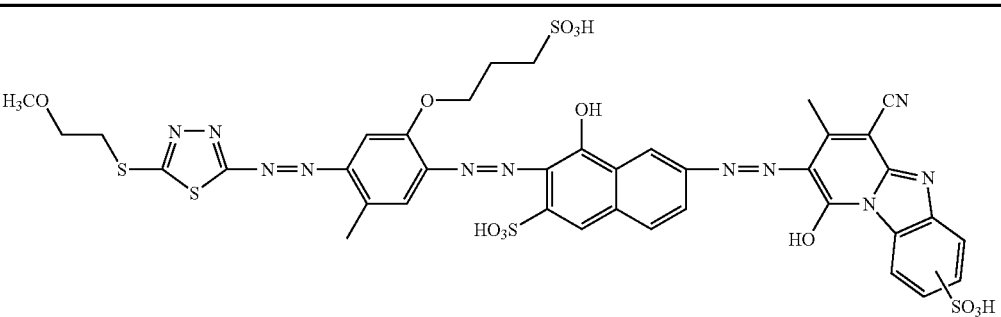 |
| 16 | 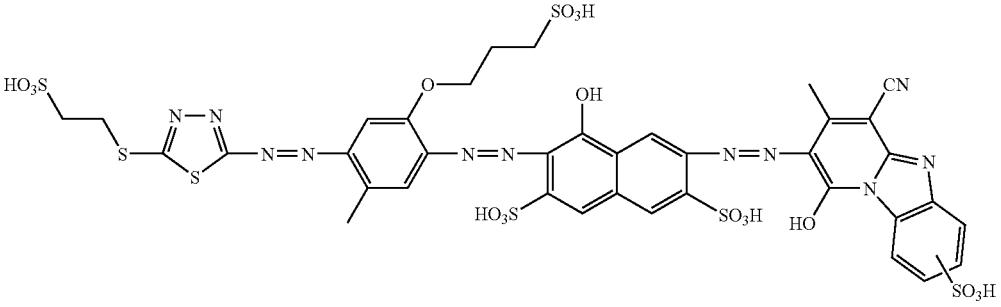 |

TABLE 4-continued

| Comp. No. | Structural Formula |
|---|---|
| 17 | |
| 18 | |
| 19 | |
| 20 | |

TABLE 4-continued

| Comp. No. | Structural Formula |
|---|---|
| 21 | (structure) |

TABLE 5

| Comp. No. | Structural Formula |
|---|---|
| 22 | (structure) |
| 23 | (structure) |
| 24 | (structure) |

TABLE 5-continued
| Comp. No. | Structural Formula |
|---|---|
| 25 | 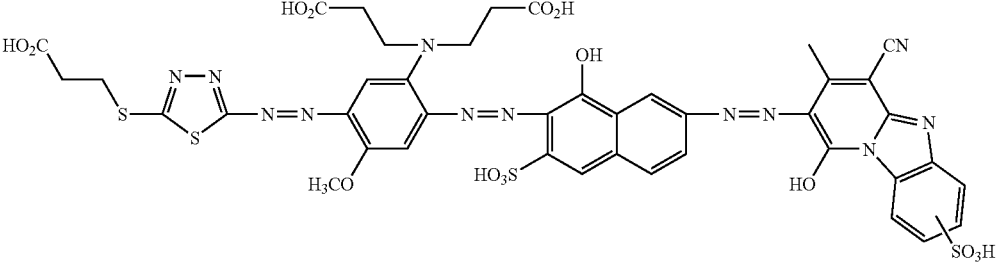 |
| 26 | 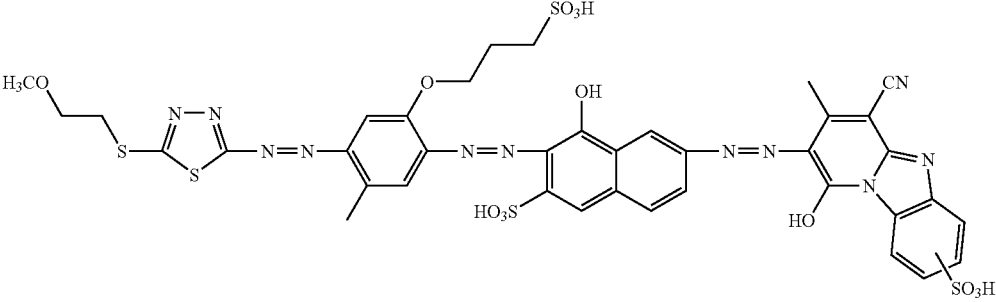 |
| 27 | 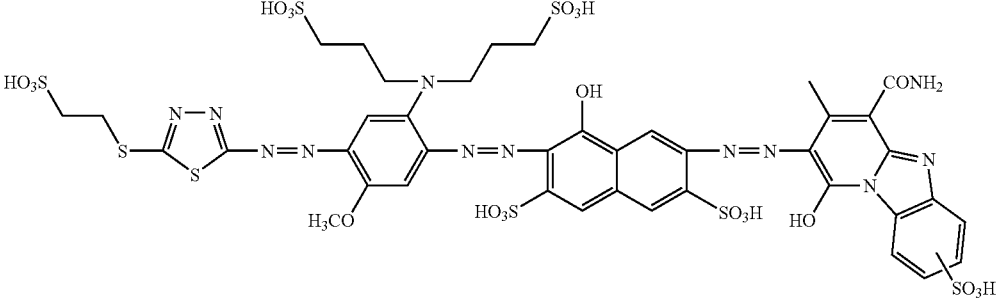 |
| 28 | 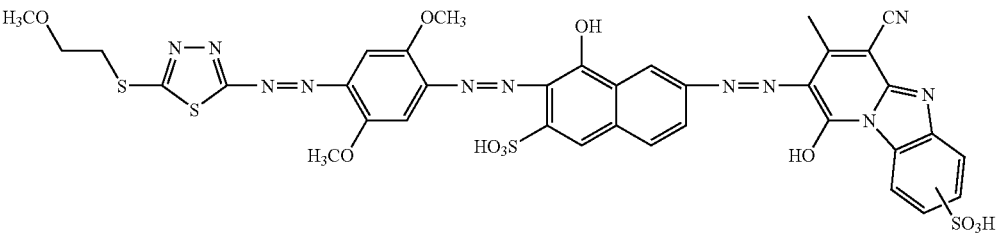 |

TABLE 6
| Comp. No. | Structural Formula |
|---|---|
| 29 | 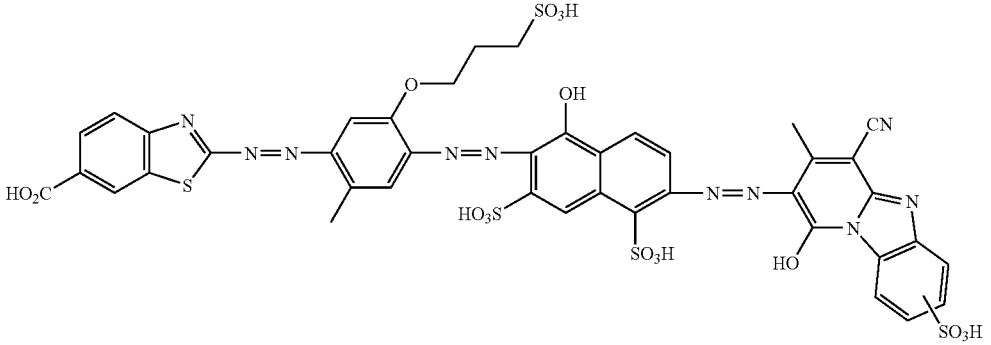 |
| 30 | 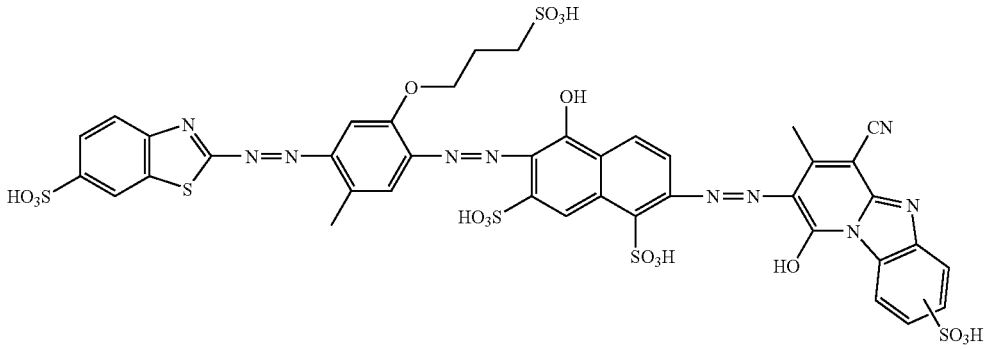 |
| 31 | 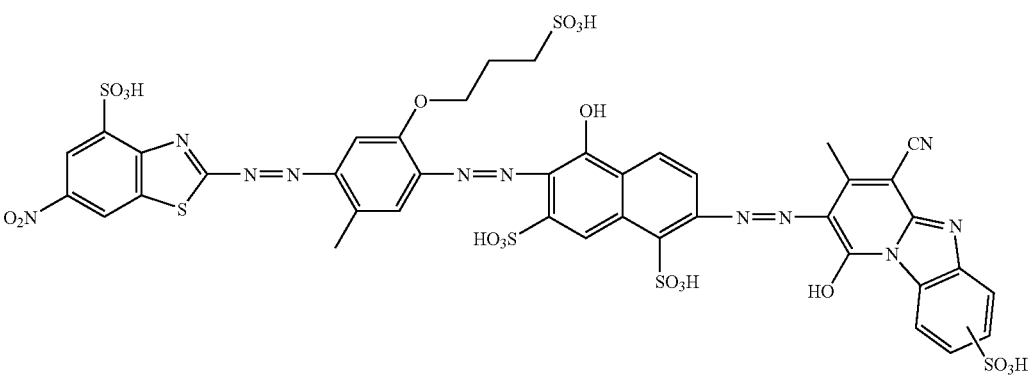 |
| 32 | 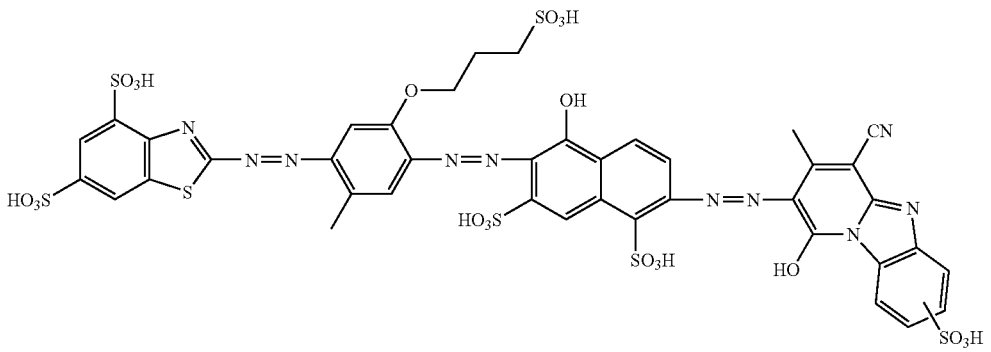 |

TABLE 6-continued

| Comp. No. | Structural Formula |
|---|---|
| 33 | |
| 34 | |
| 35 | |

TABLE 7

| Comp. No. | Structural Formula |
|---|---|
| 36 | |

TABLE 7-continued

| Comp. No. | Structural Formula |
|---|---|
| 37 | |
| 38 | |
| 39 | |
| 40 | |

TABLE 7-continued

| Comp. No. | Structural Formula |
|---|---|
| 41 | (chemical structure) |
| 42 | (chemical structure) |

TABLE 8

| Comp. No. | Structural Formula |
|---|---|
| 43 | (chemical structure) |
| 44 | (chemical structure) |

TABLE 8-continued
| Comp. No. | Structural Formula |
|---|---|
| 45 | 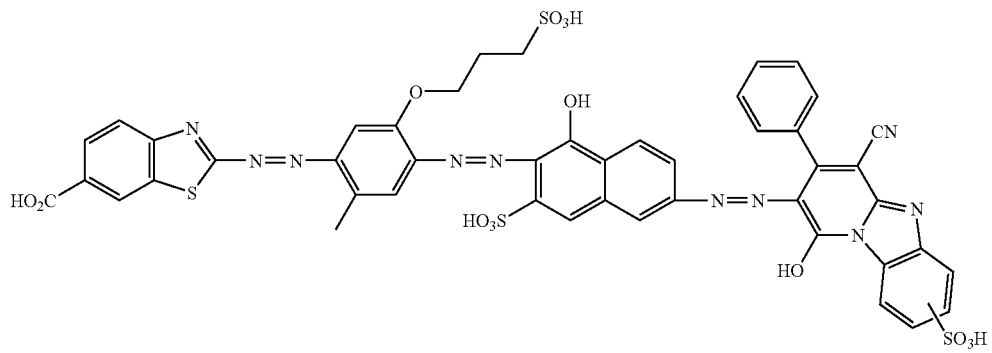 |
| 46 | 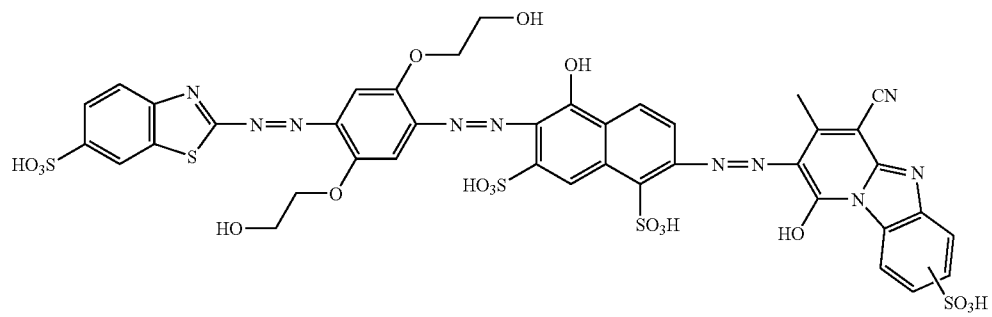 |
| 47 | 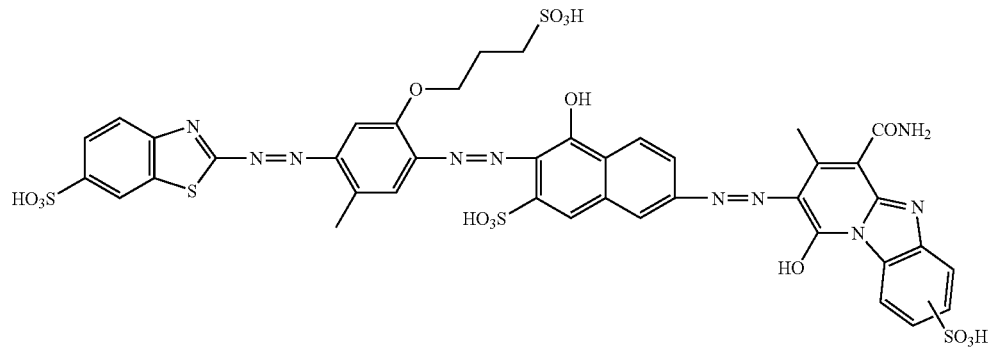 |
| 48 | 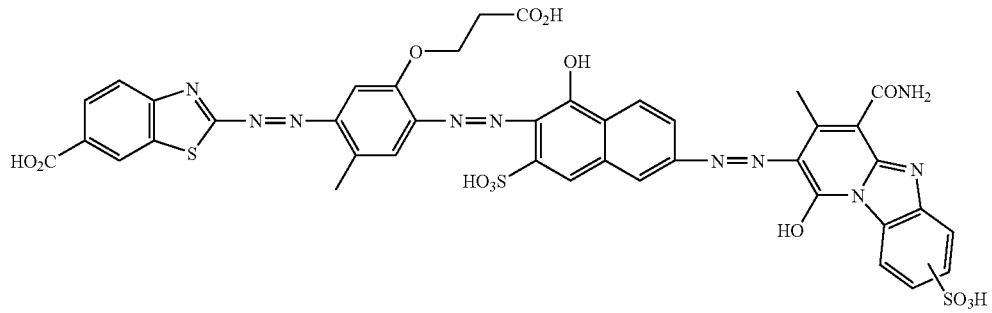 |

TABLE 8-continued

| Comp. No. | Structural Formula |
|---|---|
| 49 | (chemical structure) |

TABLE 9

| Comp. No. | Structural Formula |
|---|---|
| 50 | (chemical structure) |
| 51 | (chemical structure) |
| 52 | (chemical structure) |

TABLE 9-continued

| Comp. No. | Structural Formula |
|---|---|
| 53 | |
| 54 | |
| 55 | |
| 56 | |

TABLE 10
| Comp. No. | Structural Formula |
|---|---|
| 57 | 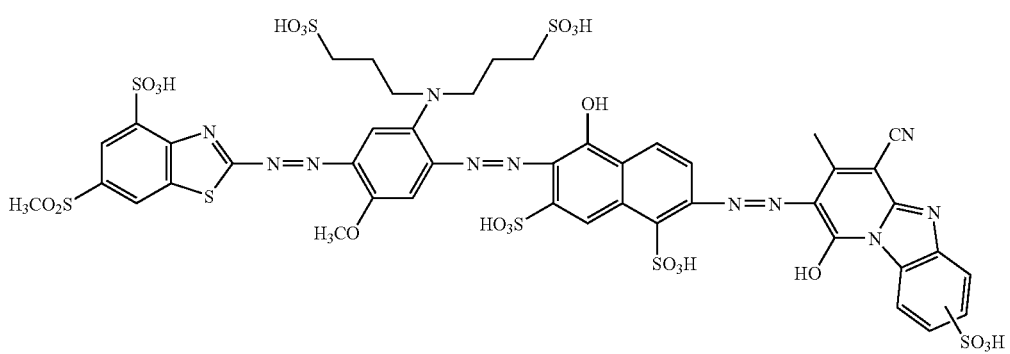 |
| 58 | 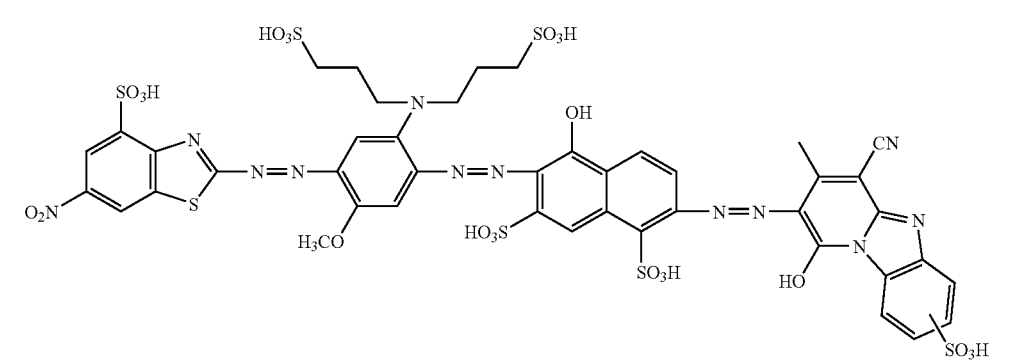 |
| 59 | 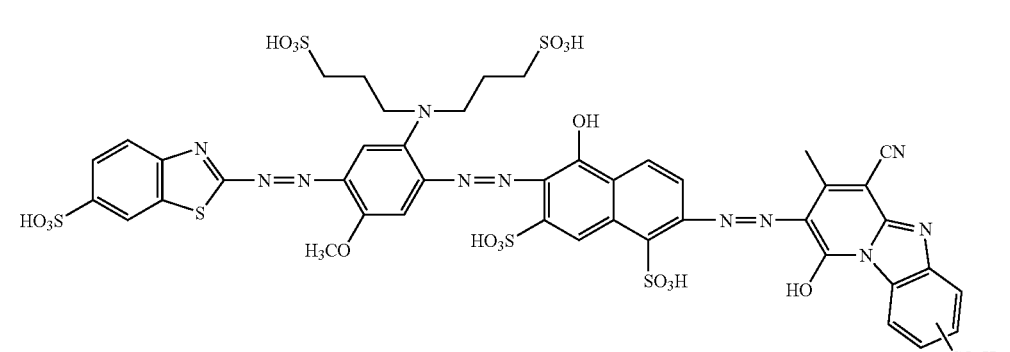 |
| 60 | 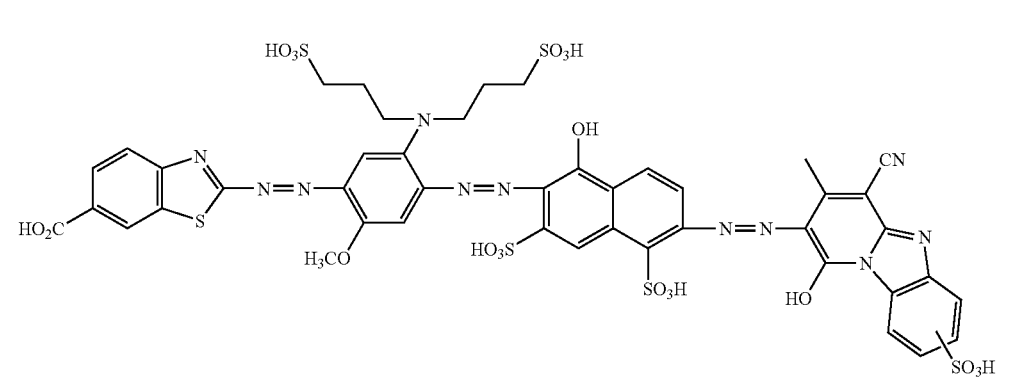 |

TABLE 10-continued

| Comp. No. | Structural Formula |
|---|---|
| 61 | (structure) |
| 62 | (structure) |
| 63 | (structure) |

TABLE 11

| Comp. No. | Structural Formula |
|---|---|
| 64 | (structure) |

TABLE 11-continued
| Comp. No. | Structural Formula |
|---|---|
| 65 | 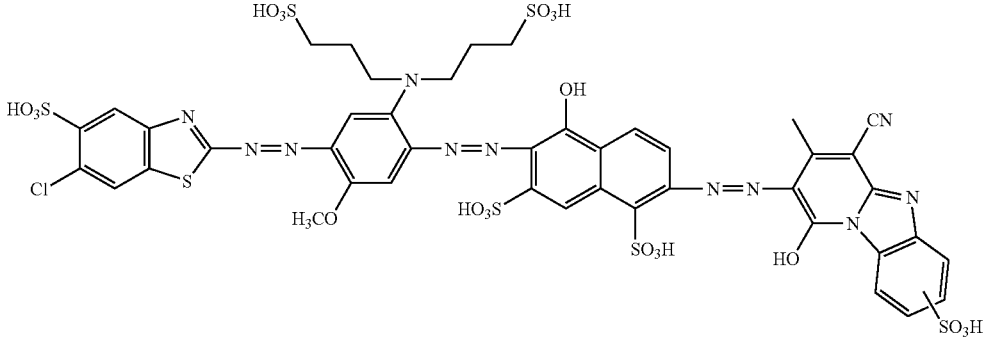 |
| 66 | 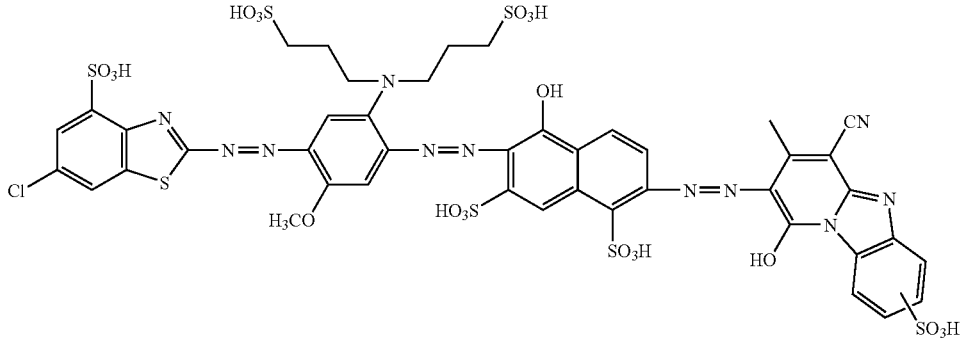 |
| 67 | 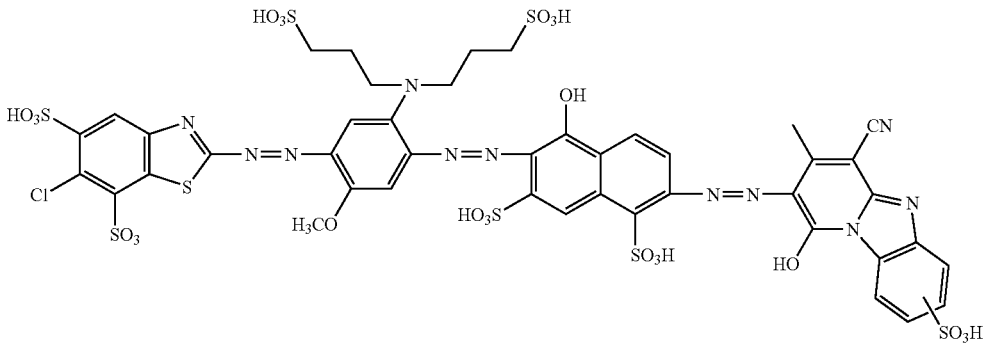 |
| 68 | 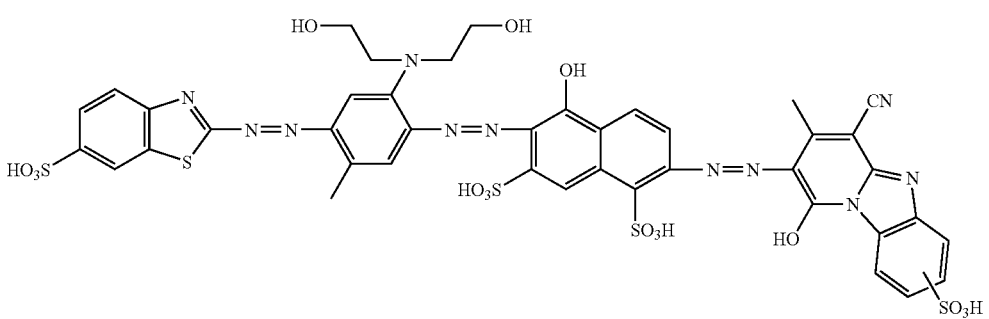 |

TABLE 11-continued

| Comp. No. | Structural Formula |
|---|---|
| 69 | (chemical structure) |
| 70 | (chemical structure) |

TABLE 12

| Comp. No. | Structural Formula |
|---|---|
| 71 | (chemical structure) |
| 72 | (chemical structure) |

TABLE 12-continued

| Comp. No. | Structural Formula |
|---|---|
| 73 | |
| 74 | |
| 75 | |
| 76 | |
| 77 | |

TABLE 13

| Comp. No. | Structural Formula |
|---|---|
| 78 | |
| 79 | |
| 80 | |
| 81 | |
| 82 | |

TABLE 13-continued
| Comp. No. | Structural Formula |
|---|---|
| 83 | 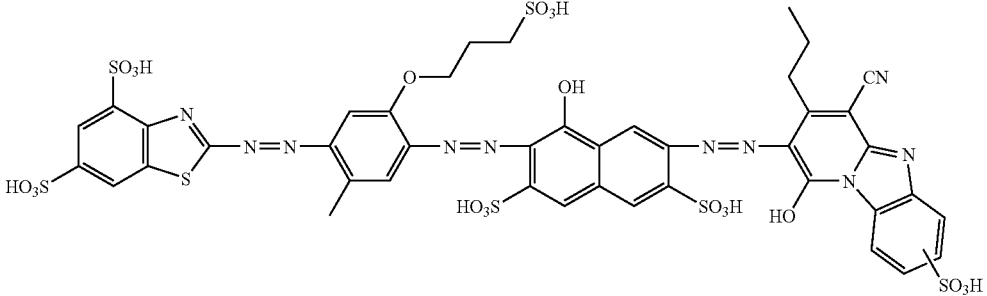 |
| 84 | 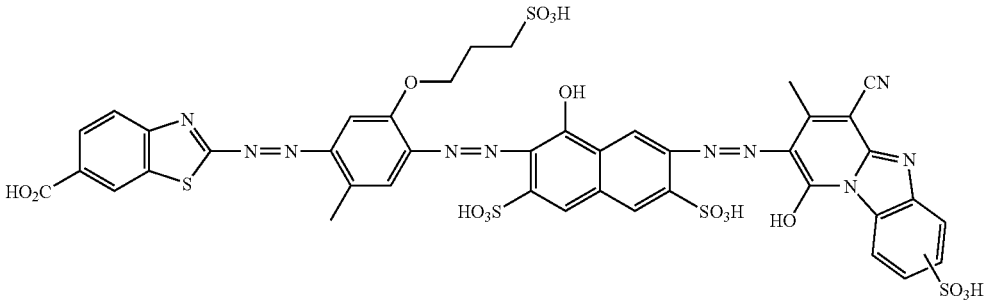 |
TABLE 14
| Comp. No. | Structural Formula |
|---|---|
| 85 | 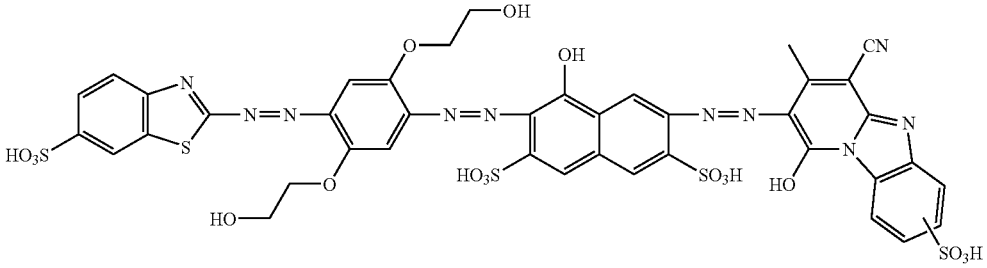 |
| 86 | 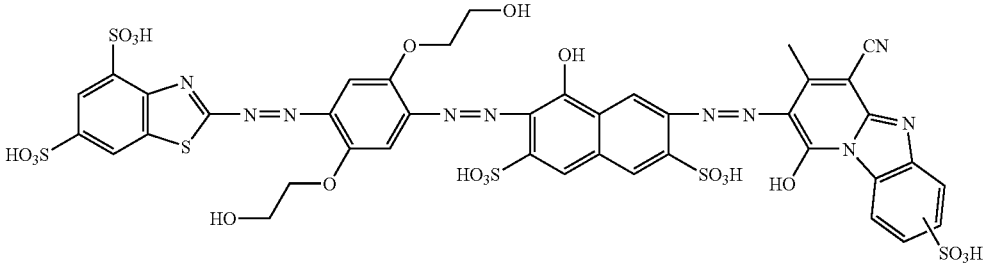 |

TABLE 14-continued

| Comp. No. | Structural Formula |
|---|---|
| 87 | |
| 88 | |
| 89 | |
| 90 | |
| 91 | |

TABLE 15

| Comp. No. | Structural Formula |
|---|---|
| 92 | |
| 93 | |
| 94 | |
| 95 | |
| 96 | |

TABLE 15-continued

| Comp. No. | Structural Formula |
|---|---|
| 97 | |
| 98 | |

TABLE 16

| Comp. No. | Structural Formula |
|---|---|
| 99 | |
| 100 | |

TABLE 16-continued

| Comp. No. | Structural Formula |
|---|---|
| 101 | |
| 102 | |
| 103 | |
| 104 | |
| 105 | |

Comp. No.: Compound Number.

The diazotization of the compound represented by the above formula (12) is carried out by a known method per se.

The diazotization is carried out in, for example, sulfuric acid, acetic acid or phosphoric acid at a temperature of, for example, −5 to 20° C. and preferably 5 to 10° C. using nitrosyl sulfuric acid. The coupling of the diazotized compound of the compound represented by the formula (12) with the compound represented by the formula (13) is also carried out in known conditions per se. The coupling reaction can be carried out in, for example, water or an aqueous organic medium (a mixture of water and a water-soluble organic solvent, and the like) at a temperature of, for example, −5 to 30° C. and preferably 10 to 30° C. The compounds represented by the formula (12) and the formula (13) are used in an approximately stoichiometric amount.

The diazotization of the compound represented by the formula (14) is also carried out by a known method per se. The diazotization is carried out in the presence of, for example, an inorganic acid such as hydrochloric acid and sulfuric acid in water or an aqueous organic medium at a temperature of, for example, −5 to 40° C. and preferably 5 to 30° C. using a nitrite, for example, an alkali metal nitrite such as sodium nitrite. The coupling of the diazotized compound of the compound represented by the formula (14) with the compound represented by the formula (15) is also carried out in known conditions per se. For example, it is advantageous that the coupling reaction is carried out in water or an aqueous organic medium at a temperature of, for example, −5 to 50° C. and preferably 10 to 30° C. and a weakly acidic to alkali pH value, for example, pH 6 to 10. It is preferred that adjustment of the above pH value is carried out by adding a base, because the diazotization reaction liquid is acidic and the inside of the reaction system is further acidified with the progress of the coupling reaction. As the base, alkali metal hydroxide such as lithium hydroxide and sodium hydroxide, alkali metal carbonate such as lithium carbonate, sodium carbonate and potassium carbonate, acetate salts such as sodium acetate, ammonia, organic amine or the like can be used. The compounds represented by the formulas (14) and (15) are used in an approximately stoichiometric amount.

The diazotization of the compound represented by the formula (16) is also carried out by a known method per se. The diazotization is carried out in the presence of, for example, an inorganic acid such as hydrochloric acid and sulfuric acid in water or an aqueous organic medium at a temperature of, for example, −5 to 40° C. and preferably 10 to 30° C. using a nitrite, for example, an alkali metal nitrite such as sodium nitrite. The coupling of the diazotized compound of the compound represented by the formula (16) with the compound represented by the formula (17) is also carried out in known conditions per se. It is advantageous to carry out in water or an aqueous organic medium at a temperature of, for example, −5 to 50° C. and preferably 10 to 30° C. and a weakly acidic to alkali pH value, for example, pH 6 to 10. The adjustment of the pH value is preferably carried out by adding a base. As the base, the same ones as described above can be used. The compounds represented by the formulas (16) and (17) are used in an approximately stoichiometric amount.

Desired salts of the trisazo compound represented by the formula (1), the formula (4) or the formula (5) of the present invention can be obtained in the form of solid or solution as follows.

For example, salting out is carried out by adding an inorganic salt or an organic cation salt which can form a desired salt, to the reaction liquid after the final coupling reaction and a desired salt of said trisazo compound can be obtained in solid form. The desired salt precipitated by salting out is separated as a solid by means of separation by filtration, and then according to necessity, purification and separation may be carried out by means of washing, recrystallization, separation by filtration or the like. In addition, a corresponding salt can be obtained in the form of solution by that aciding out is carried out by adding mineral acid such as hydrochloric acid to said reaction liquid, and said trisazo compound is separated in free acid form, washed, according to necessity, using water, acidic water or/and an aqueous organic medium to remove off an inorganic salt, and then, neutralized by a desired inorganic or organic base in an aqueous medium. Here, acidic water means water acidified by, for example, dissolving a mineral acid such as sulfuric acid and hydrochloric acid or an organic acid such as acetic acid in water. Further, the aqueous organic medium means a mixed solution of a water-miscible organic substance or/and a water-miscible organic solvent and water. Specific examples of the water-miscible organic solvent include a water-soluble organic solvent described later.

Examples of the inorganic salt include alkali metal salts such as lithium chloride, sodium chloride and potassium chloride and ammonium salts such as ammonium chloride and ammonium bromide, and examples of the organic cation salt include halogen salts of quaternary ammonium represented by the formula (11) described above. Examples of the inorganic base include, for example, alkali metal hydroxide such as lithium hydroxide, sodium hydroxide and potassium hydroxide; ammonium hydroxide; alkali metal carbonate such as lithium carbonate, sodium carbonate and potassium carbonate, and examples of the organic base include organic amine, for example, amines to be used to form quaternary ammonium ion represented by the formula (11) described above, such as diethanolamine and triethanolamine, but not limited thereto.

The ink composition of the present invention will be explained. The water-based ink composition containing the trisazo compound represented by the above formula (1) of the present invention can dye materials composed of cellulose. In addition to that, it can dye materials having a carbonamido bond and it can be widely used for dyeing leather, textile fabric and paper. Further, the typical use of the compound of the present invention includes use as an ink composition by dissolving in a liquid medium.

A reaction liquid containing the trisazo compound of the present invention represented by the above formula (1), for example, a reaction liquid containing the intended compound in Example 1 (5) described later and the like can be used directly in production of ink compositions. However, ordinary, it is preferred that the reaction liquid is dried, for example, spray-dried to separate said trisazo compound and otherwise said trisazo compound is removed by separation by filtration after said trisazo compound is precipitated by salting out by addition of an inorganic salt such as sodium chloride, potassium chloride, calcium chloride and sodium sulfate to said reaction liquid; by aciding out by addition of mineral acid such as hydrochloric acid, sulfuric acid and nitric acid; or by acid-salting out as a combination of salting out and aciding out described above, and then an ink composition is prepared using the removed trisazo compound of the present invention.

The ink composition of the present invention is a composition where the trisazo compound of the present invention is contained as a coloring matter in an amount of ordinary 0.1 to 20% by mass, preferably 1 to 10% by mass and more preferably 2 to 8% by mass and the rest is a medium mainly containing water. The ink composition of the present invention may also contain a water-soluble organic solvent in an amount of, for example, 0 to 30% by mass and an ink preparation agent in an amount of, for example, 0 to 15% by mass and preferably 0 to 10% by mass. In addition, another coloring matter may be also contained for the purpose of color toning and the like, if desired. In this regard, the pH of the ink composition is preferably pH 5 to 11 and more preferably pH 7 to 10 for the purpose of improvement of storage stability. Further, the surface tension of the ink composition is preferably 25 to 70 mN/m and more preferably 25 to 60 mN/m. Furthermore, the viscosity of the ink composition is preferably 30 mPa·s or less and more preferably 20 mPa·s or less. The pH and surface tension of the ink composition of the present invention can be appropriately adjusted by a pH adjuster and a surfactant described later.

The ink composition of the present invention can be produced by that the trisazo compound of the present invention is appropriately mixed with water or/and a water-soluble organic solvent (water-miscible organic solvent) and the like as described above, together with another coloring matter for color toning according to necessity, and then dissolved, and according to necessity, an ink preparation agent is added. Another coloring matter for color toning may be appropriately added to the trisazo compound of the present invention for the purpose of controlling black ink composition as colorless and neutral, and for the like. When this ink composition is used as an ink for inkjet printers, it is preferred that a trisazo compound of the present invention to be used has a less content of inorganic impurity such as metal cation chloride and sulfate. The inorganic impurity content is about 1% by mass or less relative to the total mass of the trisazo compound of the present invention, only as a guide. In order to produce a trisazo compound of the present invention containing less inorganic impurities, desalting treatment may be carried out by, for example, an ordinary method using a reverse osmosis membrane, or a method where a dried form or a wet cake of the trisazo compound of the present invention is stirred in a mixed solvent of alcohol and water such as methanol and the resulting precipitate is separated by filtration, dried and the like.

Specific examples of the water-soluble organic solvent to be used in preparation of the above ink composition include, for example, C1-C4 alkanol such as methanol, ethanol, propanol, isopropanol, butanol, isobutanol, secondary butanol or tertiary butanol; carboxylic acid amide such as N,N-dimethylformamide or N,N-dimethylacetoamide; lactam such as 2-pyrrolidone, N-methyl-2-pyrrolidone or N-methylpyrrolidin-2-one; cyclic urea such as 1,3-dimethylimidazolidin-2-one or 1,3-dimethylhexahydropyrimid-2-one; aliphatic ketone or aliphatic keto alcohol such as acetone, methyl ethyl ketone or 2-methyl-2-hydroxypentan-4-one; cyclic ether such as tetrahydrofuran or dioxane; mono-, oligo- or poly-alkylene glycol or thioglycol having a C2 to C6 alkylene unit such as ethylene glycol, 1,2-propylene glycol, 1,3-propylene glycol, 1,2-butylene glycol, 1,4-butylene glycol, 1,6-hexylene glycol, diethylene glycol, triethylene glycol, tetraethylene glycol, dipropylene glycol, polyethylene glycol, polypropylene glycol, thiodiglycol or dithiodiglycol; polyol (triol) such as glycerine or hexane-1,2,6-triol; mono- or di(C1-C4) alkyl ether of polyhydric alcohol such as ethylene glycol monomethyl ether, ethylene glycol monoethyl ether, diethylene glycol monomethyl ether, diethylene glycol monoethyl ether, diethylene glycol monobutyl ether (butyl carbitol), triethylene glycol monomethyl ether or triethylene glycol monoethyl ether; gamma-butyrolactone; dimethylsulfoxide; or the like. These organic solvents may be used alone, or two or more thereof are used as a combination.

The ink preparation agent to be appropriately used in preparation of the above ink composition includes, for example, an antiseptic and fungicide, a pH adjuster, a chelating agent, a rust preventive agent, a water-soluble UV absorbing agent, a water-soluble polymer compound, a coloring matter-dissolving agent, an antioxidant, a surfactant and the like. Hereinafter, these agents will be explained.

Specific examples of the fungicide include sodium dehydroacetate, sodium benzoate, sodium pyridinethion-1-oxide, ethyl p-hydroxybenzoate, 1,2-benzisothiazolin-3-one and a salt thereof, and the like. These are preferably used in an ink composition in an amount of 0.02 to 1.00% by mass.

Examples of the antiseptic agent includes, for example, organic sulfur-based, organic nitrogen sulfur-based, organic halogen-based, haloallylsulfone-based, iodopropargyl-based, N-haloalkylthio-based, nitrile-based, pyridine-based, 8-oxyquinoline-based, benzothiazole-based, isothiazoline-based, dithiol-based, pyridineoxide-based, nitropropane-based, organic tin-based, phenol-based, quaternary ammonium salt-based, triazine-based, thiazine-based, anilide-based, adamantane-based, dithiocarbamate-based, brominated indanone-based, benzyl bromoacetate-based compounds and the like. Specific examples of the organic halogen-based compound include, for example, sodium pentachlorophenol, specific examples of the pyridineoxide-based compound include, for example, sodium 2-pyridinethiol-1-oxide, and the isothiazoline-based compound includes, for example, 1,2-benzisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride and the like. Other specific examples of the antiseptic and fungicide include anhydrous sodium acetate, sodium sorbate, sodium benzoate or the like.

As the pH adjuster, any substance can be used as long as it can adjust the pH of the ink to, for example, the range of 5 to 11 without adverse effects on the ink to be prepared. Specific examples thereof include, for example, alkanolamine such as diethanolamine, triethanolamine and N-methyl diethanolamine; alkali metal hydroxide such as lithium hydroxide, sodium hydroxide and potassium hydroxide; ammonium hydroxide (ammonia water); alkali metal carbonate such as lithium carbonate, sodium carbonate, sodium hydrogen carbonate and potassium carbonate; alkali metal salt of organic acid such as potassium acetate; inorganic bases such as sodium silicate and disodium phosphate; and the like.

Specific examples of the chelating agent include, for example, sodium ethylenediaminetetraacetate, sodium nitrilotriacetate, sodium hydroxyethylethylenediaminetriacetate, sodium diethylenetriaminepentaacetate, sodium uracildiacetate or the like.

Specific examples of the rust preventive agent include, for example, hydrogen sulfite salt, sodium thiosulfate, ammonium thioglycolate, diisopropylammonium nitrite, pentaerythritol tetranitrate, dicyclohexylammonium nitrite or the like.

Examples of the water-soluble UV absorbing agent include, for example, sulfonated benzophenone-based compounds, benzotriazole-based compounds, salicylic acid-based compounds, cinnamic acid-based compounds or triazine-based compounds.

Specific examples of the water-soluble polymer compound include polyvinyl alcohol, cellulose derivatives, polyamine, polyimine or the like.

Specific examples of the coloring matter-dissolving agent include, for example, epsilon-caprolactam, ethylene carbonate, urea or the like.

Examples of the antioxidant include, for example, various organic-based and metal complex-based antifading agents for use. Examples of the above organic-based antifading agent include hydroquinones, alkoxyphenols, dialkoxyphenols, phenols, anilines, amines, indanes, chromans, alkoxyanilines, heterocyclic rings or the like.

Examples of the surfactant include, for example, known surfactants such as anion-based, cation-based, nonion-based surfactants or the like.

Examples of the anionic surfactant include alkyl sulfonate, alkylcarboxylate, alpha-olefin sulfonate, polyoxyethylene alkyl ether acetate, N-acylamino acid and a salt thereof, N-acylmethyltaurine salt, alkylsulfate polyoxyalkyl ether sulfate, alkylsulfate polyoxyethylene alkyl ether phosphate, rosin acid soap, castor oil sulfate, lauryl alcohol sulfate, alkylphenol type phosphoric acid ester, alkyl type phosphoric acid ester, alkylallylsulfonate, diethyl sulfosuccinate, diethylhexyl sulfosuccinate, dioctyl sulfosuccinate or the like.

The cationic surfactant includes 2-vinylpyridine derivatives, poly(4-vinylpyridine) derivatives or the like.

Specific examples of the amphoteric surfactant include lauryldimethylaminoacetic acid betaine, 2-alkyl-N-carboxymethyl-N-hydroxyethyl imidazolinium betaine, coconut oil fatty acid amide propyldimethylaminoacetic acid betaine, polyoctylpolyaminoethylglycine, imidazoline derivatives or the like.

Specific examples of the nonionic surfactant include ether-based such as polyoxyethylene nonylphenyl ether, polyoxyethylene octylphenyl ether, polyoxyethylene dodecylphenyl ether, polyoxyethylene oleyl ether, polyoxyethylene lauryl ether and polyoxyethylene alkyl ether; ester-based such as polyoxyethylene oleic acid, polyoxyethylene oleate ester, polyoxyethylene distearate ester, sorbitan laurate, sorbitan monostearate, sorbitan monooleate, sorbitan sesquioleate, polyoxyethylene monooleate and polyoxyethylene stearate; acetylene glycol (alcohol)-based ones such as 2,4,7,9-tetramethyl-5-decyne-4,7-diol, 3,6-dimethyl-4-octyne-3,6-diol and 3,5-dimethyl-1-hexyn-3-ol; and the like. Specific examples thereof include, for example, Surfynol® 104, 105, 82 and 465, Olfine® STG and the like which are trade names and manufactured by Nissin Chemical Industry Co., Ltd.

These ink preparation agents are used alone or as a mixture thereof.

The ink composition of the present invention is obtained by mixing and stirring the above components in any order. The obtained ink composition may be filtered using a membrane filter, if desired, in order to remove impurities. In addition, another coloring matter having a different hue may be mixed besides the trisazo compound of the present invention in order to control the tint of black in the ink composition. In that case, another coloring matter of black having another hue, yellow, orange, brown, scarlet, red, magenta, violet, blue, navy, cyan, green or the like can be mixed for use.

The ink composition of the present invention can be used in various fields and suitable for water-based ink for writing tools, water-based printing ink, information recording ink and the like. It is particularly suitable as an ink (composition) for inkjet, and suitably used in the inkjet printing method of the present invention mentioned below.

Next, the inkjet printing method of the present invention will be explained. The inkjet printing method of the present invention is characterized in that recording is performed using the above ink composition of the present invention. In the inkjet printing method of the present invention, recording is performed on a record-receiving material by discharging the above ink composition of the present invention as droplets by inkjet and by adhering them on the record-receiving material. The ink nozzle and the like to be used for inkjet are not particularly limited and can be appropriately selected according to the purpose and the inkjet method.

As the inkjet method, a known method, for example, a charge control method where ink is discharged using electrostatic attractive force; a drop-on-demand method (pressure pulse method) using oscillating pressure of piezoelectric elements; an acoustic inkjet method where an electric signal is converted to an acoustic beam, which is then irradiated on ink and the radiation pressure is used to discharge the ink; a thermal inkjet method where ink is heated to form bubbles and the generated pressure is used, namely bubble jet® method; and the like can be employed.

In addition, the above inkjet printing method includes a method where a number of a small volume of ink having a low coloring matter concentration (coloring matter content), called photo ink, are injected; a method where a plurality of inks having a substantially same hue and a different concentration of coloring matter are used to improve image quality; a method where colorless and transparent ink is used; and the like.

The colored product of the present invention includes any product colored with the above trisazo compound of the present invention, and the colored product of the present invention can be obtained by coloring various articles such as a record-receiving material with the ink composition of the present invention containing the above trisazo compound. More preferable are products colored with the ink composition of the present invention by inkjet printing method using an inkjet printer.

The material to be colored is not particularly limited and includes, for example, communication sheets such as paper and film, fiber and cloth (such as cellulose, nylon and wool), leather, substrates for color filters, and the like.

Among them, the communication sheet is preferably ones subjected to surface treatment, specifically ones providing with an ink receiving layer on the substrate of paper, synthetic paper, film or the like. The ink receiving layer is provided by, for example, a method where a cation polymer is impregnated in or coated on the above substrate; a method where the above substrate surface is coated with a porous white inorganic substance which can absorb coloring matter in ink such as porous silica, aluminasol and special ceramics, together with a hydrophilic polymer such as polyvinyl alcohol and polyvinylpyrrolidone; or the like.

The communication sheet provided with such an ink receiving layer is ordinary called inkjet special paper (film), glossy paper (film) or the like. Specific examples thereof include Professional Photopaper, Super Photopaper or Matte Photopaper (which are all manufactured by Canon Inc.); Photo Paper (glossy), PM MATTE PAPER or CRISPIA® (which are all manufactured by Seiko-Epson Corporation); Advanced Photo Paper, Premium Plus Photo Paper, Premium Glossy Film or Photo Paper (which are all manufactured by Hewlett Packard Japan, Ltd.); PhotoLike® QP (which is manufactured by KONICA Corporation); and the like, which are all trade names and available as a commercial product. In addition, plain paper can be obviously used.

It is known that discoloration or fading of images recorded on a sheet whose surface is coated particularly with a porous white inorganic substance, among the above communication sheets, becomes more evident by ozone gas. However, the ink composition of the present invention has excellent ozone gas fastness and therefore has particularly great effects when inkjet printed on a record-receiving material.

In order to record on a record-receiving material such as a communication sheet by the inkjet printing method of the present invention, for example, a container containing the above ink composition is placed in a predetermined position in an inkjet printer and ink is discharged by an ordinary method to record on a record-receiving material.

In the inkjet printing method of the present invention, a black ink composition of the present invention can be used in combination with ink compositions of other colors, for example, known magenta, cyan, yellow, and according to necessity, green, blue (or violet) and red (or orange).

Each color ink composition is filled in each container and each container is placed in a predetermined position in an inkjet printer together with an container of a black ink composition of the present invention and used together with the black ink composition of the present invention for inkjet printing.

The trisazo compound of the present invention has excellent water-solubility, and in addition, the ink composition of the present invention containing this compound is free from crystal precipitation, change in physical properties, change in hue and the like even after storage for a long period of time, and thus it has good storage stability.

Further, the ink composition containing the trisazo compound of the present invention as a coloring matter is suitable for inkjet printing and for writing tools.

When printing is performed on an information recording sheet, particularly inkjet special paper using said ink composition, the printed images have high print density and additionally are excellent in fastnesses, particularly in ozone gas fastness and light fastness.

EXAMPLES

Hereinafter, the present invention will be specifically explained with reference to the Examples but not limited to the following Examples.

In the context, "part(s)" and "%" are based on mass unless otherwise specifically noted.

In addition, in the formulas below, acidic functional groups such as a sulfo group and a carboxy group are shown in free acid form.

Further, any of the pH values and reaction temperatures described below shows a value measured in each reaction system.

Furthermore, the maximum absorption wavelength (λmax) of a synthesized compound is measured in an aqueous solution of pH 7 to 8 and each value of the measured compounds is shown in Examples.

In this regard, any of the synthesized trisazo compounds of the present invention shows a solubility of 100 g/L or more in water.

Example 1

(1)

In 90 parts of methanol, 10.6 parts of 2-amino-5-mercapto-1,3,4-thiadiazole were dissolved, and then 18.6 parts of 2-bromoethanesulfonic acid, 3.5 parts of sodium hydroxide and 14.6 parts of water were added there.

The resulting solution was stirred at 55 to 60° C. for 6 hours. After cooling to 20° C., the precipitated solid was separated by filtration to obtain 16.4 parts of a compound represented by the following formula (18).
Formula (18):

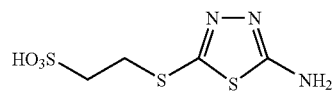
(18)

(2)

In 30 parts of 85% phosphoric acid, 3.6 parts of the compound represented by the above formula (18) were suspended, and 5.7 parts of 40% nitrosyl sulfuric acid were added dropwise to said suspension under stirring at 5 to 10° C. for about 10 minutes. The reaction was carried out for 3 hours to obtain a reaction liquid.

On the other hand, 3.3 parts of a compound represented by the following formula (19) and 0.4 parts of sulfamic acid were added to 30 parts of water, and then the pH was adjusted to 5.0 to 5.5 with sodium hydroxide to obtain an aqueous solution.

To the obtained aqueous solution, the above diazo reaction liquid was added dropwise at a reaction temperature of 20 to 30° C. over about 10 minutes.

After completion of the dropwise addition, the mixture was stirred at the same temperature for 2 hours. To the resulting reaction liquid, sodium hydroxide was added to adjust the pH to 0.7 to 1.2. The precipitated solid was separated by filtration to obtain a wet cake containing a compound represented by the following formula (20).

In this regard, the compound represented by the following formula (19) was obtained by the method described in JP 2004-083492 A.

Formula (19) and Formula (20):

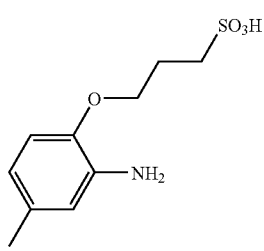

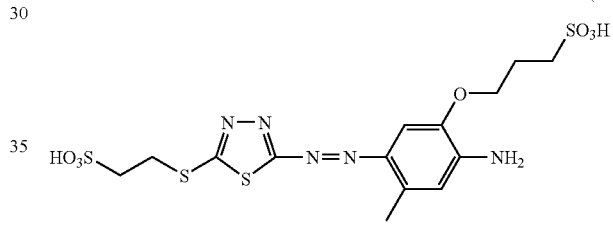

(3)
To 35 parts of water, 3.5 parts of a compound represented by the following formula (21) were added, and then the pH was adjusted to 7.5 to 8.0 with sodium hydroxide to obtain an aqueous solution containing a compound represented by the formula (21).

On the other hand, under stirring, the wet cake containing the compound represented by the formula (20) obtained in Example 1 (2) was suspended in 120 parts of water and the pH was adjusted to 6.0 to 6.5 with sodium hydroxide to obtain an aqueous solution. To the obtained aqueous solution, 3.2 parts of 35% hydrochloric acid were added, and then 2.1 parts of a 40% aqueous sodium nitrite solution were added dropwise there at a reaction temperature of 15 to 20° C. over about 5 minutes. The reaction was carried out for 1 hour to obtain a diazo reaction liquid.

The obtained diazo reaction liquid was added dropwise to the former-obtained aqueous solution containing the compound represented by the formula (21) at a reaction temperature of 20 to 30° C. over 20 minutes. In the meantime, sodium carbonate was added to the reaction system to maintain the pH at 7.0 to 8.0.

After completion of the dropwise addition, the mixture was stirred at the same temperature for 2 hours. Salting out was carried out by addition of sodium chloride. The precipitated solid was separated by filtration. A wet cake containing a compound represented by the following formula (22) was obtained.

Formula (21) and Formula (22):

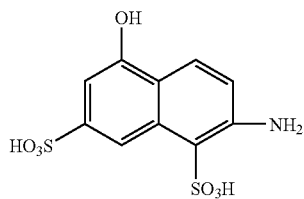
(21)

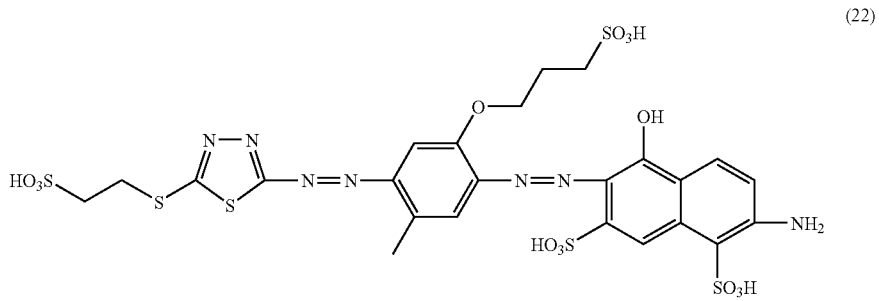
(22)

(4)

In ethanol, 2-(cyanomethyl)benzimidazole and ethyl acetoacetate were reacted by heating in the presence of sodium methoxide. Aciding out was carried out by addition of dilute hydrochloric acid to obtain a compound represented by the following formula (23). To 128 parts of 6% fuming sulfuric acid, 19.8 parts of said compound obtained were slowly added at 15 to 25° C. After the addition, the mixture was stirred at the same temperature for 2 hours and then the resulting reaction liquid was added dropwise to 380 parts of ice water over about 10 minutes. The precipitated crystals were separated by filtration and dried to obtain 21.4 parts of a compound represented by the following formula (24).

Formula (23) and Formula (24):

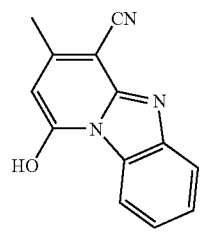
(23)

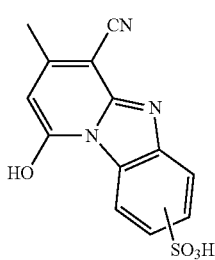
(24)

(5)

To 55 parts of water, 2.4 parts of the compound represented by the above formula (24) were added, and then the pH was adjusted to 7.5 to 8.0 with sodium hydroxide to obtain an aqueous solution containing the compound represented by the formula (24).

On the other hand, under stirring, the wet cake containing the compound represented by the formula (22) obtained in Example 1 (3) was dissolved in 220 parts of water and 2.5 parts of 35% hydrochloric acid were added there. Then, 1.5 parts of a 40% aqueous sodium nitrite solution were added dropwise there at a reaction temperature of 20 to 25° C. over about 5 minutes. The reaction was carried out for 1 hour to obtain a diazo reaction liquid.

The obtained diazo reaction liquid was added dropwise to the former-obtained aqueous solution containing the compound represented by the above formula (24) at a reaction temperature of 20 to 30° C. over 30 minutes. In the meantime, sodium carbonate was added to the reaction system to maintain the pH at 7.0 to 8.0.

After completion of the dropwise addition, the mixture was stirred at the same temperature for 2 hours to obtain a reaction liquid containing an intended compound represented by the following formula (25). Salting out was carried out by addition of sodium chloride to said reaction liquid. The precipitated solid was separated by filtration to obtain a wet cake. The obtained wet cake was dissolved in 160 parts of water and 280 parts of methanol were added there for crystallization. The precipitated solid was separated by filtration to obtain a wet cake. The obtained wet cake was again dissolved in 130 parts of water and 400 parts of methanol were added for crystallization. The precipitated solid was separated by filtration and dried to obtain 8.9 parts of a compound represented by the following formula (25) of the present invention (Compound No. 2 in Table 2) as sodium salt.

λmax: 588 nm.

Formula (25):

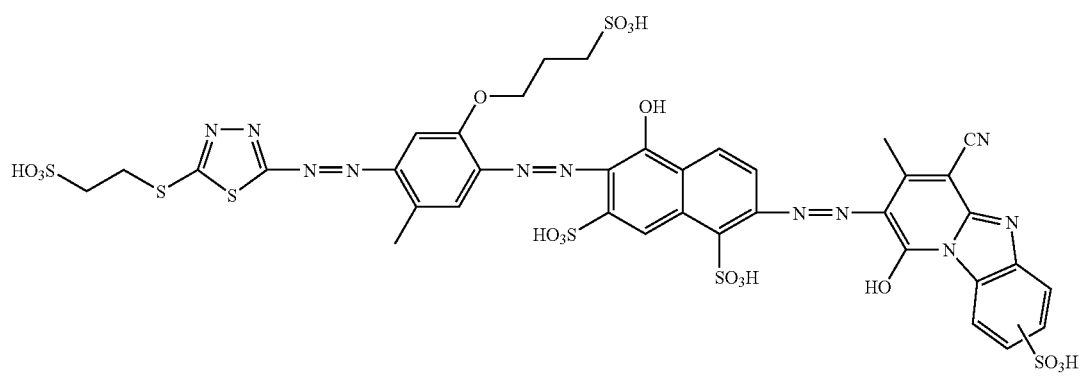

Example 2

In the same manner as in Example 1 except that 2.9 parts of 2-aminobenzothiazole-6-carboxylic acid was used instead of 3.6 parts of the compound represented by the above formula (18) in Example 1 (2), 8.7 parts of a compound represented by the following formula (26) of the present invention (Compound No. 29 in Table 6) were obtained as sodium salt.

λmax: 591 nm.

Formula (26):

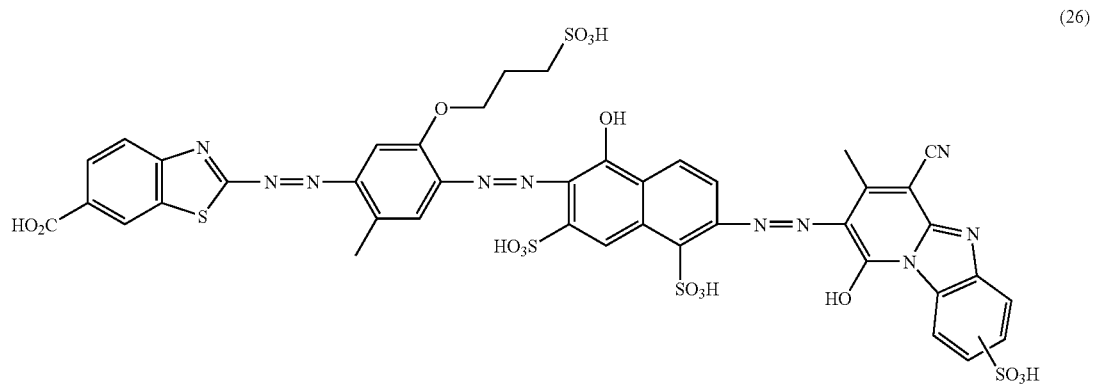

Example 3

(1)

In 21 parts of 50% sulfuric acid, 3.5 parts of 2-aminobenzothiazole-6-sulfonic acid were suspended. Under stirring at 5 to 10° C., 5.8 parts of 40% nitrosyl sulfuric acid were added dropwise over about 10 minutes. The reaction was carried out for 3 hours to obtain a diazo reaction liquid.

On the other hand, 3.3 parts of the compound represented by the above formula (19) and 0.4 parts of sulfamic acid were added to 30 parts of water and then the pH was adjusted to 5.0 to 5.5 with sodium hydroxide to obtain an aqueous solution.

The above diazo reaction liquid was added dropwise to the obtained aqueous solution at a reaction temperature of 20 to 30° C. over about 10 minutes.

After completion of the dropwise addition, the mixture was stirred at the same temperature for 2 hours. Thereto, sodium hydroxide was added to adjust the pH to 0.7 to 1.2. The precipitated solid was separated by filtration to obtain a wet cake containing a compound represented by the following formula (27).

Formula (27):

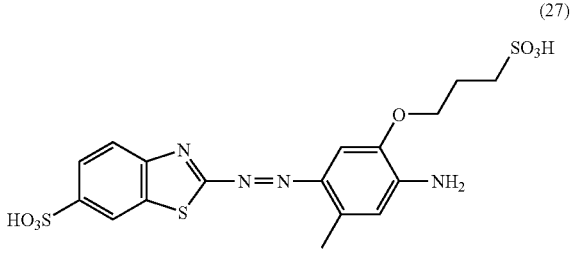

(2)

In the same manner as in Example 1 except that the above wet cake containing the compound represented by the formula (27) was used instead of the wet cake containing the compound represented by the formula (20) in Example 1 (3), 8.8 parts of a compound represented by the following formula (28) of the present invention (Compound No. 30 in Table 6) were obtained as sodium salt.

λmax: 593 nm.

Formula (28):

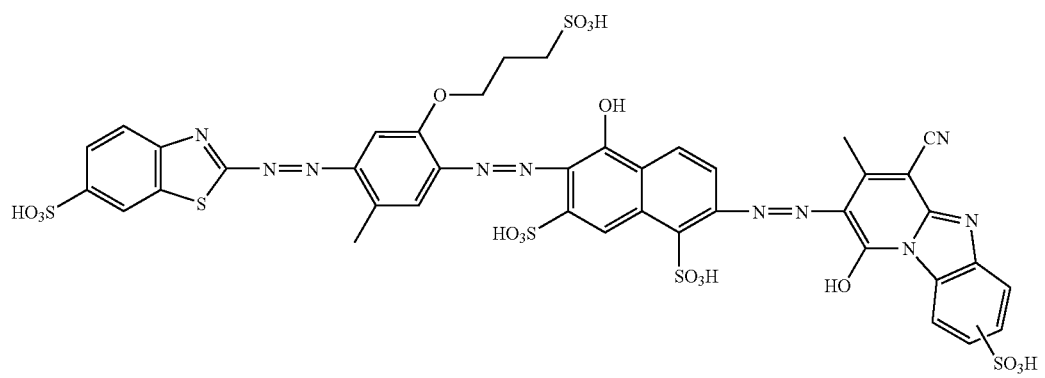

Example 4

(1)

To 25 parts of 30% fuming sulfuric acid, 9.8 parts of 2-amino-6-nitro benzothiazole were slowly added at 20 to 25° C. After the addition, the temperature of said mixed liquid was raised to 100° C. and the mixed liquid was stirred at the same temperature for 6 hours. The resulting reaction solution was added dropwise to 100 parts of ice water over about 15 minutes. The precipitated crystals were separated by filtration and dried to obtain 11.7 parts of a compound represented by the following formula (29).

Formula (29):

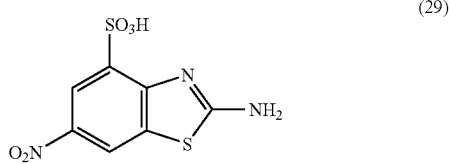

(2)

In the same manner as in Example 3 except that 4.1 parts of the compound represented by the above formula (29) was used instead of 3.5 parts of 2-aminobenzothiazole-6-sulfonic acid in Example 3 (1), 9.2 parts of a compound represented by the following formula (30) of the present invention (Compound No. 31 in Table 6) were obtained as sodium salt.

λmax: 600 nm.

Formula (30):

Example 5

(1)

To 20 parts of 30% fuming sulfuric acid, 7.0 parts of 2-aminobenzothiazole-6-sulfonic acid were slowly added at 20 to 25° C. After the addition, the temperature of said mixed liquid was raised to 100° C. and the mixed liquid was stirred at the same temperature for 5 hours. The resulting reaction liquid was added dropwise to 80 parts of ice water over about 15 minutes. The precipitated crystals were separated by filtration and dried to obtain 8.7 parts of a compound represented by the following formula (31).

Formula (31):

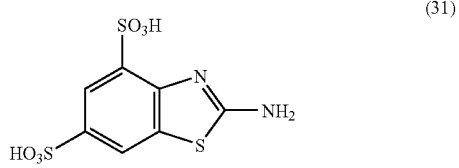

(2)

In the same manner as in Example 3 except that 4.7 parts of the compound represented by the above formula (31) was used instead of 3.5 parts of 2-aminobenzothiazole-6-sulfonic acid in Example 3 (1), 9.4 parts of a compound represented by the following formula (32) of the present invention (Compound No. 32 in Table 6) were obtained as sodium salt.

λmax: 604 nm.

Formula (32):

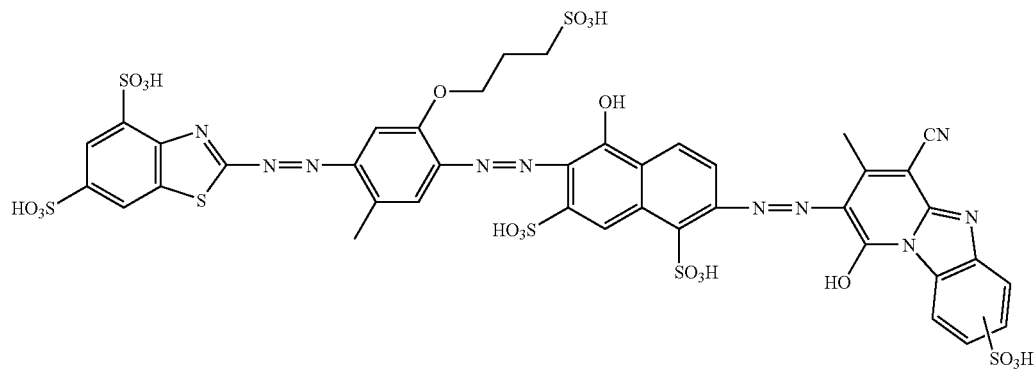

Example 6

(1)
To 20 parts of 30% fuming sulfuric acid, 7.0 parts of 2-amino-6-methylsulfonylbenzothiazole were slowly added at 20 to 25° C. After the addition, the temperature of said mixed liquid was raised to 100° C., and the mixed liquid was stirred at the same temperature for 5 hours and then added dropwise to 80 parts of ice water over about 15 minutes. The precipitated crystals were separated by filtration and dried to obtain 8.7 parts of a compound represented by the following formula (33).

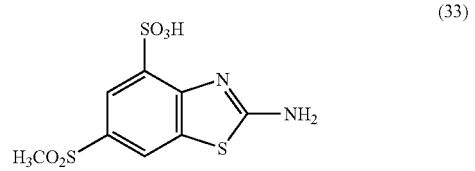

(2)
In the same manner as in Example 3 except that 4.6 parts of the compound represented by the above formula (33) were used instead of 3.5 parts of 2-aminobenzothiazole-6-sulfonic acid in Example 3 (1), 9.3 parts of a compound represented by the following formula (34) (Compound No. 33 in Table 6) of the present invention were obtained as sodium salt.
λmax: 595 nm.
Formula (34):

Example 7

(1)
To 16 parts of 15% fuming sulfuric acid, 5.0 parts of 2-amino-6-methoxybenzothiazole were slowly added at 15 to 25° C. After the addition, said mixed liquid was stirred at the same temperature for 2 hours and then added dropwise to 60 parts of ice water over about 10 minutes. The precipitated crystals were separated by filtration and dried to obtain 6.4 parts of a mixture of a compound represented by the following formula (35) and a compound represented by the following formula (36).
Formula (35) and Formula (36):

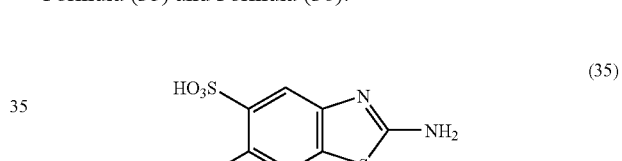

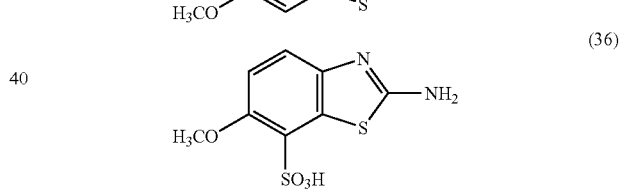

(2)
In the same manner as in Example 3 except that 3.9 parts of the mixture of the compounds represented by the above for-

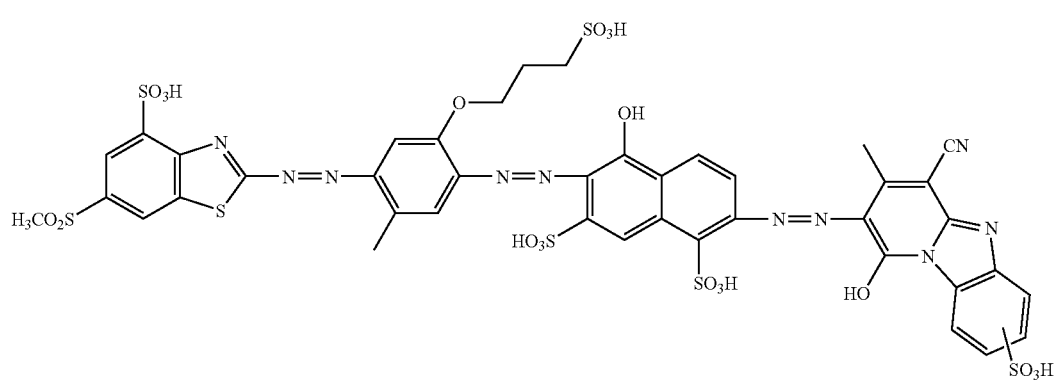

mula (35) and the above formula (36) were used instead of 3.5 parts of 2-aminobenzothiazole-6-sulfonic acid in Example 3 (1), 9.1 parts of a mixture of a compound represented by the following formula (37) (Compound No. 34 in Table 6) and a compound represented by the following formula (38) (Compound No. 35 in Table 6) of the present invention were obtained as sodium salt.

λmax of the mixture: 593 nm.

Formula (37) and Formula (38):

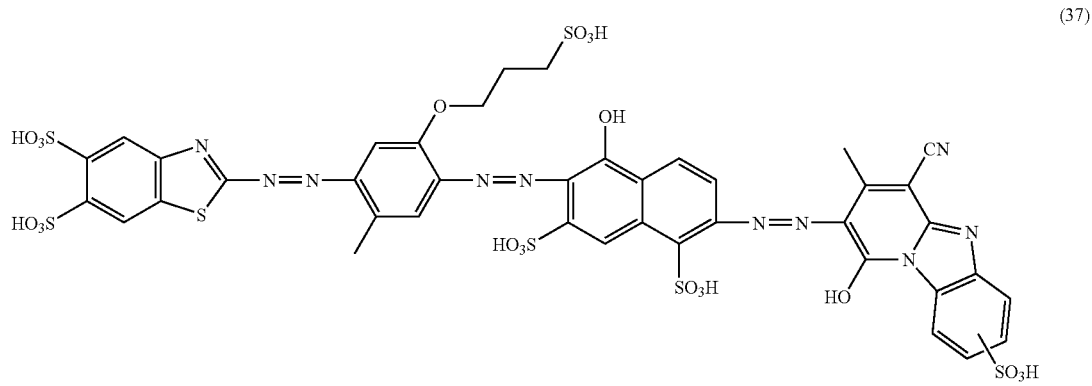
(37)

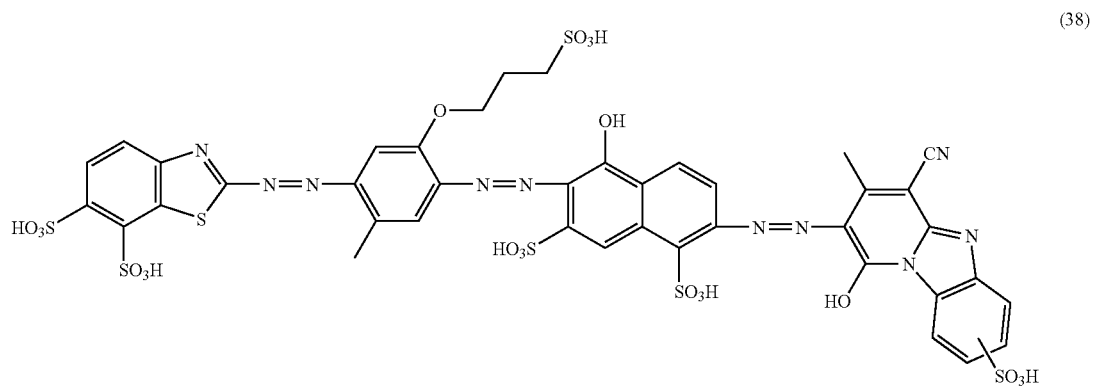
(38)

Example 8

(1)

To 21 parts of 20% fuming sulfuric acid, 7.2 parts of 2-amino-6-chloro benzothiazole were slowly added at 15 to 25° C. After the addition, the temperature of said mixed liquid was raised to 100° C. and the mixed liquid was stirred at the same temperature for 3 hours and then added dropwise to 80 parts of ice water over about 15 minutes. The precipitated crystals were separated by filtration and dried to obtain 9.8 parts of a mixture of compounds represented by the following formula (39) and the following formula (40).

Formula (39) and Formula (40):

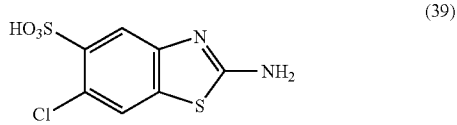
(39)

-continued

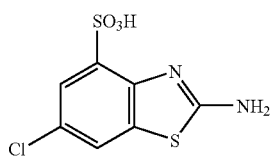
(40)

(2)

In the same manner as in Example 3 except that 4.0 parts of the mixture of compounds represented by the above formula (39) and the above formula (40) were used instead of 3.5 parts of 2-aminobenzothiazole-6-sulfonic acid in Example 3 (1), 9.2 parts of a mixture of a compound represented by the following formula (41) (Compound No. 41 in Table 7) and a compound represented by the following formula (42) (Compound No. 42 in Table 7) of the present invention were obtained as sodium salt.

λmax of the mixture: 591 nm.

Formula (41) and Formula (42):

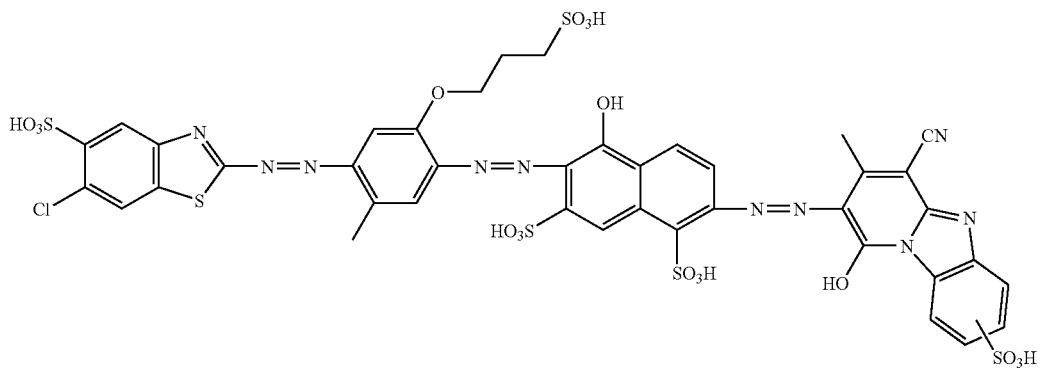

(41)

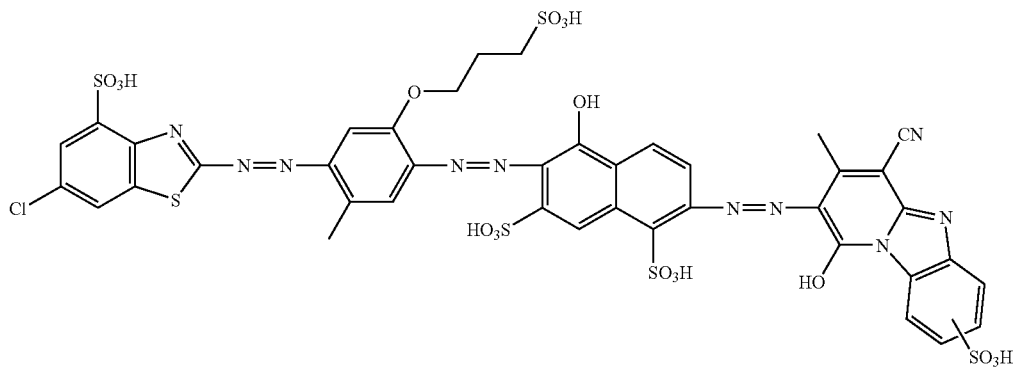

(42)

Example 9

(1)

The same operation as in Example 3 (1) was conducted to obtain a wet cake containing a compound represented by the above formula (27).

(2)

To 37 parts of water, 3.7 parts of a compound represented by the following formula (43) were added, and then the pH was adjusted to 7.5 to 8.0 with sodium hydroxide to obtain an aqueous solution containing the compound represented by the formula (43).

On the other hand, under stirring, the wet cake containing the compound represented by the above formula (27) obtained in the above (1) was suspended in 120 parts of water and the pH was adjusted 6.0 to 6.5 with sodium hydroxide to obtain an aqueous solution containing the compound represented by the formula (27). To the obtained aqueous solution, 3.4 parts of 35% hydrochloric acid were added, and then 2.1 parts of a 40% aqueous sodium nitrite solution were added dropwise at a reaction temperature of 15 to 20° C. over about 5 minutes. The reaction was carried out for 1 hour to obtain a diazo reaction liquid.

The obtained diazo reaction liquid was added dropwise to the former-obtained aqueous solution containing the compound represented by the following formula (43) at a reaction temperature of 20 to 30° C. for 20 minutes. In the meantime, sodium carbonate was added to the reaction system to maintain the pH at 7.0 to 8.0.

After completion of the dropwise addition, the mixture was stirred at the same temperature for 2 hours. Salting out was carried out by addition of sodium chloride. The precipitated solid was separated by filtration. A wet cake containing a compound represented by the following formula (44) was obtained.

Formula (43) and Formula (44):

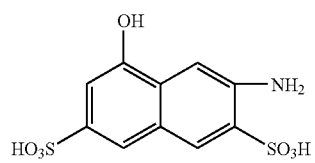

(43)

(44)

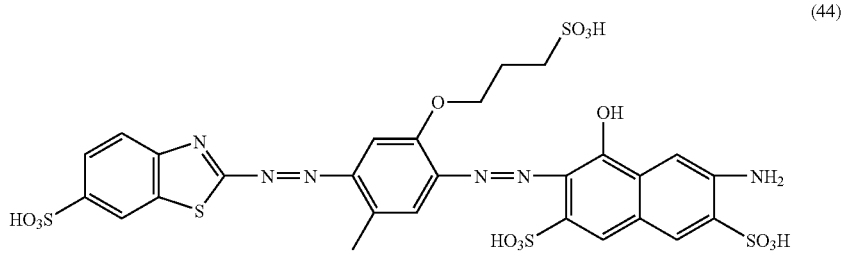

(3)

To 55 parts of water, 2.4 parts of the compound represented by the above formula (24) were added, and then the pH was adjusted to 7.5 to 8.0 with sodium hydroxide to obtain an aqueous solution.

On the other hand, under stirring, the wet cake containing the compound represented by the above formula (44) obtained in Example 9 (2) was dissolved in 210 parts of water, and 2.5 parts of 35% hydrochloric acid were added to the solution. Then, 1.5 parts of a 40% aqueous sodium nitrite solution were added dropwise to the resulting solution at a reaction temperature of 20 to 25° C. over about 5 minutes. The reaction was carried out for 1 hour to obtain a diazo reaction liquid.

The obtained diazo reaction liquid was added dropwise to the former-obtained aqueous solution containing the compound represented by the above formula (24) at a reaction temperature of 20 to 30° C. over 30 minutes. In the meantime, sodium carbonate was added to the reaction system to maintain the pH at 7.0 to 8.0.

After completion of the dropwise addition, the mixture was stirred at the same temperature for 2 hours. Salting out was carried out by addition of sodium chloride thereto. The precipitated solid was separated by filtration to obtain a wet cake. The obtained wet cake was dissolved in 140 parts of water. Thereto, 300 parts of methanol were added for crystallization, and the precipitated solid was separated by filtration to obtain a wet cake. The obtained wet cake was again dissolved in 120 parts of water. Thereto, 400 parts of methanol was again added for crystallization, and the precipitated solid was separated by filtration and dried to obtain 8.9 parts of a compound represented by the following formula (45) of the present invention (Compound No. 75 in Table 12) as sodium salt.

λmax: 606 nm.

Formula (45)

Example 10

(A) Preparation of Ink

The components described below were mixed to obtain a black ink composition of the present invention, and then foreign substances were filtered off using a 0.45 μm membrane filter. Hereinafter, the obtained ink composition was referred to as "ink".

In addition, ion-exchanged water was used as water. In ink preparation, the pH of ink was adjusted to pH 7 to 9 with sodium hydroxide and after that, ion-exchanged water was added to make the total amount 100 parts.

TABLE 17

| | |
|---|---|
| Each compound obtained in Examples 1 and 3 to 8 | 3.5 parts |
| Glycerine | 5.0 parts |
| Urea | 5.0 parts |
| N-Methyl-2-pyrrolidone | 4.0 parts |
| Isopropylalcohol | 3.0 parts |
| Butyl carbitol | 2.0 parts |
| Surfactant (trade name: Surfynol$^{RTM}$ 104, manufactured by Nissin Chemical Industry Co., Ltd.) | 0.1 part |
| Water + sodium hydroxide | 77.4 parts |
| Total | 100.0 parts |

In Table 17, the following tests conducted using the inks containing the compounds obtained in the above Examples 1 and 3 to 8 are Examples 10 to 16, respectively. The aqueous black ink of the present invention is free from precipitation during storage and no change in physical properties was caused after storage for a long period of time.

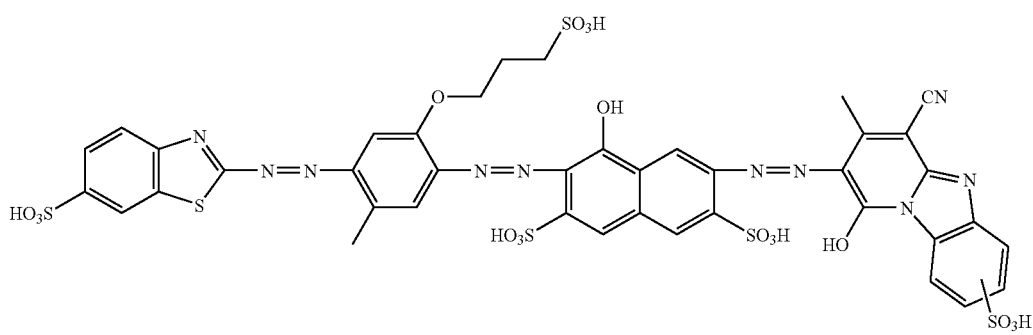

(45)

Comparative Example 1

As a black coloring matter for comparison, an ink for comparison was prepared in the same composition as in Table 17 except that a coloring matter of the following formula (46) disclosed in Example 1 of Patent Literature 3 was used instead of the compounds in Examples. The following test conducted using this ink is Comparative Example 1.

Formula (46)

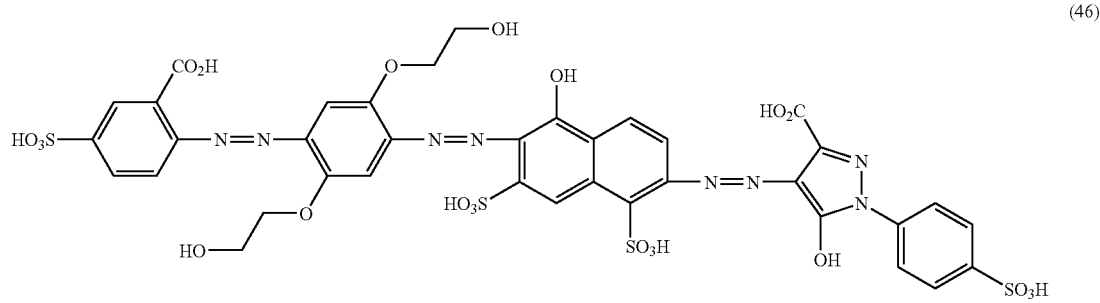

(46)

(B) Inkjet Printing

Using each ink obtained in the above manner, inkjet printing was performed on three kinds of information recording sheet (inkjet special paper), glossy paper 1 [trade name: Professional Photopaper PR-101, manufactured by Canon Inc.], glossy paper 2 [trade name: Photo Paper CRISPIA (highly glossy), manufactured by Seiko-Epson Corporation], glossy paper 3 [trade name: Advanced Photo Paper (glossy), manufactured by Hewlett-Packard Development Company] by an inkjet printer (trade name: PIXUS® iP4100) manufactured by Canon Inc.

In printing, an image pattern was made so that several gradations in reflection density were obtained, and black printed matter was obtained.

(C) Evaluation of Recorded Image

Printed images obtained using the inks of Example 10 to 16 and Comparative Example 1 were evaluated for change in image density before and after light fastness test and ozone gas fastness test, respectively.

Using a colorimeter (trade name: SpectroEye®) manufactured by GRETAG-MACBETH, change in printed image density was measured by measuring, after the test, the gradation part where the reflection density, D value, was nearest to 1.0 on each printed image before the test.

In this regard, the tests were conducted on glossy papers 1, 2 and 3, and the test results are shown in Table 18.

The details of the test methods are as follows.

1) Ozone Gas Fastness Test

Using an ozone weatherometer manufactured by Suga Test Instruments Co., Ltd., each printed image was left for 24 hours under the conditions of an ozone concentration of 10 ppm, a humidity of 60% RH and a temperature of 24° C. After completion of the test, each printed image was measured by the above colorimeter and the coloring matter residual rate was calculated from the formula (reflection density after test/reflection density before test)×100 (%). The test results are evaluated according to the following criteria.

○: Residual rate is 70% or more.
Δ: Residual rate is 60% or more and less than 70%.
×: Residual rate is less than 60%.

2) Light Fastness Test

Using a low temperature xenon weatherometer (trade name: XL75) manufactured by Suga Test Instruments Co., Ltd., each printed image described above was irradiated for 96 hours under the conditions of a luxilluminance of 100,000, a humidity of 60% RH and a temperature of 24° C. and then measured using the above colorimeter, and the coloring matter residual rate of each image was calculated from the formula (reflection density after test/reflection density before test)×100 (%). The test results are evaluated according to the following criteria.

○: Residual rate is 85% or more.
Δ: Residual rate is 80% or more and less than 85%.
×: Residual rate is less than 80%.

TABLE 18

| | Ozone gas fastness | Light fastness |
|---|---|---|
| Example 10 [Formula (25)] | | |
| Glossy paper 1 | ○ | ○ |
| Glossy paper 2 | ○ | Δ |
| Glossy paper 3 | ○ | ○ |
| Example 11 [Formula (28)] | | |
| Glossy paper 1 | ○ | ○ |
| Glossy paper 2 | ○ | ○ |
| Glossy paper 3 | ○ | ○ |
| Example 12 [Formula (30)] | | |
| Glossy paper 1 | ○ | ○ |
| Glossy paper 2 | ○ | ○ |
| Glossy paper 3 | ○ | ○ |
| Example 13 [Formula (32)] | | |
| Glossy paper 1 | ○ | Δ |
| Glossy paper 2 | ○ | ○ |
| Glossy paper 3 | ○ | ○ |
| Example 14 [Formula (34)] | | |
| Glossy paper 1 | ○ | ○ |
| Glossy paper 2 | ○ | ○ |
| Glossy paper 3 | ○ | ○ |
| Example 15 [Mixture of Formulas (37) and (38)] | | |
| Glossy paper 1 | ○ | ○ |
| Glossy paper 2 | ○ | ○ |
| Glossy paper 3 | ○ | ○ |
| Example 16 [Mixture of Formulas (41) and (42)] | | |
| Glossy paper 1 | ○ | ○ |
| Glossy paper 2 | ○ | ○ |
| Glossy paper 3 | ○ | ○ |
| Comparative Example 1 [Formula (46)] | | |
| Glossy paper 1 | X | X |
| Glossy paper 2 | X | X |
| Glossy paper 3 | X | Δ |

As is clear from the results of Table 18, Examples have better results than Comparative Example 1 when the results of ozone gas fastness test on each glossy paper are compared between the printed images of Examples 10 to 16 and the printed image of Comparative Example 1. Specifically, the coloring matter residual rate of Comparative Example 1 is less than 60% on any glossy paper while the coloring matter residual rate of Examples 10 to 16 of the present invention is 70% or more on any glossy paper. Herewith, it is found that Examples are extremely excellent in ozone gas fastness compared with Comparative Example.

In addition, there are similarly differences observed in light fastness test. Specifically, Examples 11, 12, 14 to 16 show coloring matter residual rates of 85% or more even when used on any glossy paper. Example 10 shows a coloring matter residual rate of 85% or more when used on glossy papers 1 and 3, and a coloring matter residual rate of 80% or more and less than 85% when used on glossy paper 2. Example 13 shows a coloring matter residual rate of 85% or more when used on glossy papers 2 and 3, and a coloring matter residual rate of 80% or more and less than 85% when used on glossy paper 1.

On the other hand, Comparative Example 1 shows a coloring matter residual rate of 80% or more and less than 85% when used on glossy paper 3, while it shows a coloring matter residual rate of less than 80% when used on glossy papers 1 and 2. From the results, it is found that Examples are also extremely excellent in light fastness compared with Comparative Example. Further, any of the print densities of the recorded images using the inks of Example 10 to 16 is higher than that of Comparative Example 1.

Judging from the above results, the fastnesses of the printed images obtained from the inks containing the trisazo compound of the present invention is extremely excellent compared with that obtained from the conventional trisazo compound used in Comparative Example 1. The trisazo compound of the present invention is a balanced dye which is extremely excellent in ozone gas fastness required particularly in inkjet-printed images and also in light fastness.

INDUSTRIAL APPLICABILITY

The ink composition containing the azo compound of the present invention is suitably used as a black ink liquid for inkjet printing and for writing tools.

The invention claimed is:
1. A trisazo compound represented by the following formula (1) or a salt thereof:

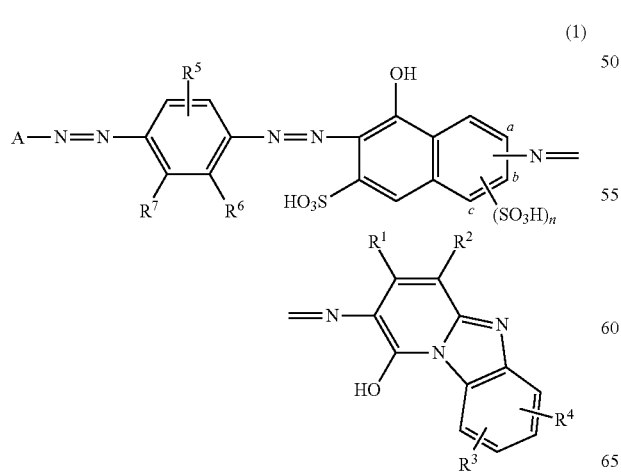

wherein, n is 0 or 1,
$R^1$ represents a carboxy group; an unsubstituted C1-C4 alkyl group; a C1-C4 alkyl group substituted by a carboxy group; an unsubstituted phenyl group; or a phenyl group substituted by a sulfo group,
$R^2$ represents a cyano group; a carbamoyl group; or a carboxy group,
$R^3$ and $R^4$ each independently represent a hydrogen atom; a chlorine atom; a sulfo group; an unsubstituted C1-C4 alkyl group; or an unsubstituted C1-C4 alkoxy group,
$R^5$ to $R^7$ each independently represent a hydrogen atom; a chlorine atom; a hydroxy group; a sulfo group; a carboxy group; a sulfamoyl group; a carbamoyl group; an unsubstituted C1-C4 alkyl group; an unsubstituted C1-C4 alkoxy group; a C1-C4 alkoxy group substituted by a hydroxy group, an unsubstituted C1-C4 alkoxy group, a hydroxy C1-C4 alkoxy group, a sulfo group or a carboxy group; a mono- or di-unsubstituted C1-C4 alkylamino group; a mono- or di-C1-C4 alkylamino group substituted by a hydroxy group, a sulfo group or a carboxy group; an unsubstituted C1-C4 alkylcarbonylamino group; a C1-C4 alkylcarbonylamino group substituted by a hydroxy group or a carboxy group; an N'-(unsubstituted C1-C4 alkyl)ureide group; an N'-(a C1-C4 alkyl substituted by a hydroxy group, a sulfo group or a carboxy group)ureide group; an unsubstituted phenylamino group; a phenylamino group where the benzene ring is substituted by a chlorine atom, an unsubstituted C1-C4 alkyl group, a nitro group, a sulfo group or a carboxy group; an unsubstituted benzoylamino group; a benzoylamino group where the benzene ring is substituted by a chlorine atom, an unsubstituted C1-C4 alkyl group, a nitro group, a sulfo group or a carboxy group; an unsubstituted phenylsulfonylamino group; or a phenylsulfonylamino group where the benzene ring is substituted by a chlorine atom, an unsubstituted C1-C4 alkyl group, a nitro group, a sulfo group or a carboxy group,
the substitution position of the azo group of the naphthalene ring to which the benzimidazolopyridone ring substituted by $R^1$ to $R^4$ is bonded via the azo group is a or b; and the substitution position of the sulfo group by which said naphthalene ring is substituted is b or c, provided that the position is not overlapped with the substitution position of the above azo group, and
the group A is a substituted heterocyclic group represented by the following formula (2) or (3):

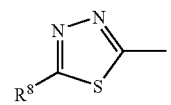

wherein, $R^8$ represents a mercapto group; an unsubstituted C1-C4 alkylthio group; or a C1-C4 alkylthio group substituted by a hydroxy group, an unsubstituted C1-C4 alkoxy group, a hydroxy C1-C4 alkoxy group, a sulfo group or a carboxy group

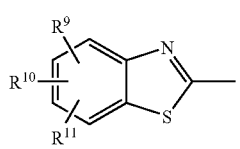

(wherein, $R^9$ to $R^{11}$ each independently represent a hydrogen atom; a chlorine atom; a carboxy group; a sulfo group; a nitro group; a hydroxy group; a carbamoyl group; a sulfamoyl group; an unsubstituted C1-C4 alkyl group; an unsubstituted C1-C4 alkoxy group; a C1-C4 alkoxy group substituted by a hydroxy group, an unsubstituted C1-C4 alkoxy group, a sulfo group or a carboxy group; an unsubstituted C1-C4 alkylsulfonyl group; a C1-C4 alkylsulfonyl group substituted by a hydroxy group, a sulfo group or a carboxy group; an unsubstituted phenylsulfonyl group; or a phenylsulfonyl group where the benzene ring is substituted by a chlorine atom, an unsubstituted C1-C4 alkyl group, a nitro group, a sulfo group or a carboxy group.

2. The trisazo compound or a salt thereof according to claim 1, which is represented by the following formula (4):

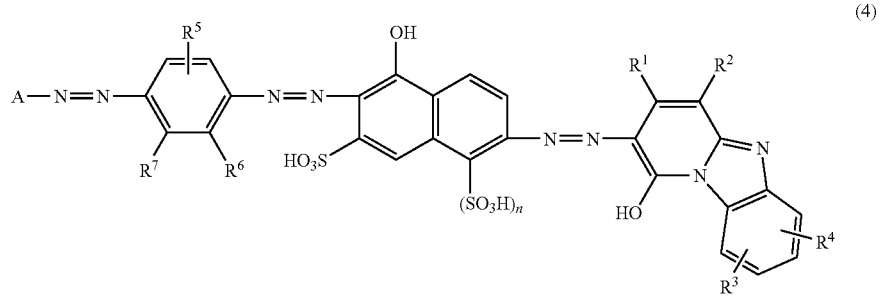

(4)

wherein, n, the group A and $R^1$ to $R^7$ have the same meanings as in the formula (1).

3. The trisazo compound or a salt thereof according to claim 1, which is represented by the following formula (5):

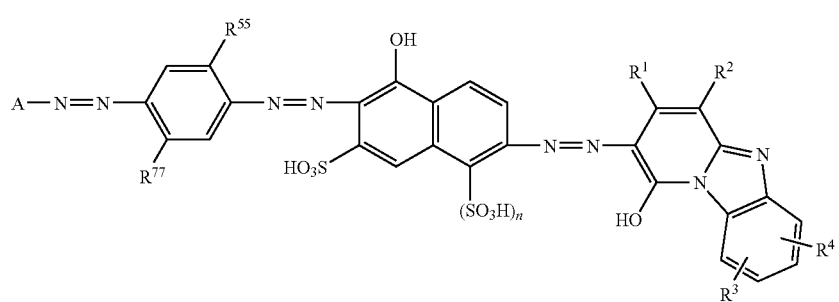

(5)

wherein, n, the group A and $R^1$ to $R^4$ have the same meanings as in the formula (1), $R^{55}$ represents a sulfo C1-C4 alkoxy group, and $R^{77}$ represents a hydrogen atom, a methyl group or an ethyl group.

4. The trisazo compound or a salt thereof according to claim 1 or 3, wherein the group A is represented by the formula (2), $R^8$ is a sulfo C1-C4 alkylthio group or a carboxy C1-C4 alkylthio group.

5. The trisazo compound or a salt thereof according to claim 1 or 3, wherein the group A is represented by the formula (3), $R^9$ to $R^{11}$ are each independently a hydrogen atom, a chlorine atom, a carboxy group, a sulfo group, a nitro group, an unsubstituted C1-C4 alkyl group, an unsubstituted C1-C4 alkoxy group or an unsubstituted C1-C4 alkylsulfonyl group.

6. The trisazo compound or a salt thereof according to claim 1, wherein $R^1$ is a methyl group, $R^2$ is a cyano group or a carbamoyl group, $R^3$ is a hydrogen atom, and $R^4$ is a sulfo group.

7. The trisazo compound or a salt thereof according to claim 1 or 3, wherein the group A is a substituted heterocyclic group represented by the formula (2) or the formula (3), $R^8$ of the formula (2) is a sulfo C1-C4 alkylthio group or a carboxy C1-C4 alkylthio group, and $R^9$ to $R^{11}$ of the formula (3) are each independently a hydrogen atom, a chlorine atom, a carboxy group, a sulfo group, a nitro group, an unsubstituted C1-C4 alkyl group, an unsubstituted C1-C4 alkoxy group or an unsubstituted C1-C4 alkylsulfonyl group.

8. The trisazo compound or a salt thereof according to claim 7, wherein $R^1$ is a methyl group, $R^2$ is a cyano group or a carbamoyl group, $R^3$ is a hydrogen atom and $R^4$ is a sulfo group.

9. The trisazo compound or a salt thereof according to claim 5, wherein n is 1, $R^1$ is a methyl group, $R^2$ is a cyano group, $R^3$ is a hydrogen atom, $R^4$ is a sulfo group, $R^5$ is a sulfopropoxy group, $R^6$ is a hydrogen atom, $R^7$ is a methyl group, the group A is the formula (3), $R^9$ to $R^{11}$ are each independently a hydrogen atom, a chlorine atom, a carboxy group, a sulfo group, a nitro group, a methyl group, a methoxy group or a methylsulfonyl group.

10. An ink composition comprising at least one kind of the trisazo compound or a salt thereof according to claim 1 or 3 as a coloring matter.

11. A method for inkjet printing comprising adhering an ink composition containing at least one kind of the trisazo compound or a salt thereof according to claim 1 on a record-receiving material by inkjet.

12. The method for inkjet printing according to claim 11, wherein the record-receiving material in the inkjet printing is a communication sheet.

13. The method for inkjet printing according to claim 12, wherein the communication sheet is a sheet containing a porous white inorganic substance.

14. An inkjet printer comprising a container containing an ink composition containing at least one kind of the trisazo compound or a salt thereof according to claim 1.

15. A colored product colored with the trisazo compound or a salt thereof according to claim 1.

16. The trisazo compound or a salt thereof according to claim 1, wherein:
$R^1$ is an unsubstituted C1-C4 alkyl group or an unsubstituted phenyl group,
$R^2$ is a cyano group or a carbamoyl group,
$R^3$ is a hydrogen atom,
$R^4$ is a sulfo group,
$R^5$ to $R^7$ are each independently a hydrogen atom; a sulfo group; an unsubstituted C1-C4 alkyl group; an unsubstituted C1-C4 alkoxy group; a C1-C4 alkoxy group substituted by a hydroxy group, a carboxy group or a sulfo group; an unsubstituted C1-C4 dialkylamino group; a dialkylamino group substituted by a carboxy group, a sulfo group or a hydroxy group; an unsubstituted C1-C4 alkylcarbonylamino group; N'-C1-C4 alkylureide group substituted by a sulfo group or a carboxy group; or an unsubstituted benzoylamino group,
$R^8$ is a C1-C4 alkylthio group substituted by a sulfo group or a carboxy group,
$R^9$ to $R^{11}$ are each independently a hydrogen atom; a chlorine atom; a carboxy group; a sulfo group; a nitro group; an unsubstituted C1-C4 alkyl group; an unsubstituted C1-C4 alkoxy group; or unsubstituted C1-C4 alkylsulfonyl group, and
any two of $R^5$ to $R^7$ are groups other than a hydrogen atom.

17. The trisazo compound or a salt thereof according to claim 7, wherein n is 1, $R^1$ is an alkyl group having 1 to 4 carbon atoms, $R^2$ is a cyano group, any one of $R^3$ and $R^4$ is a hydrogen atom and the other is a sulfo group, $R^8$ of the formula (2) is a sulfo C1-C4 alkylthio group, $R^9$ to $R^{11}$ of the formula (3) are each independently a hydrogen atom, a chlorine atom, a sulfo group, a nitro group, an unsubstituted C1-C4 alkoxy group or an unsubstituted C1-C4 alkylsulfonyl group, at least one of $R^9$ to $R^{11}$ is a sulfo group, either of the rest is a hydrogen atom and the other is a hydrogen atom or a group other than a hydrogen atom.

18. The trisazo compound or a salt thereof according to claim 17, wherein the group A is the formula (3), at least one of $R^9$ to $R^{11}$ is a sulfo group, either of the rest is a hydrogen atom and the other is a group other than a hydrogen atom.

19. The trisazo compound or a salt thereof according to claim 18, wherein the group other than a hydrogen atom is a sulfo group or an unsubstituted C1-C4 alkoxy group.

* * * * *